US011278245B2

(12) United States Patent
Pekonen et al.

(10) Patent No.: US 11,278,245 B2
(45) Date of Patent: Mar. 22, 2022

(54) ENHANCING OPTICAL CARDIAC ACTIVITY MEASUREMENT

(71) Applicant: Polar Electro Oy, Kempele (FI)

(72) Inventors: Elias Pekonen, Oulu (FI); Matti Orava, Oulu (FI); Olli Komulainen, Oulu (FI); Seppo Korkala, Kempele (FI); Pekka Rytky, Oulu (FI); Mika Rahja, Oulu (FI); Tuomas Hartikainen, Oulu (FI); Lauri Lumme, Oulu (FI)

(73) Assignee: Polar Electro Oy, Kempele (FI)

( * ) Notice: Subject to any disclaimer, the term of this patent is extended or adjusted under 35 U.S.C. 154(b) by 148 days.

(21) Appl. No.: 16/111,203

(22) Filed: Aug. 23, 2018

(65) Prior Publication Data
US 2019/0059821 A1 Feb. 28, 2019

(30) Foreign Application Priority Data

Aug. 25, 2017 (WO) ................. PCT/EP2017/071428

(51) Int. Cl.
*A61B 5/00* (2006.01)
*A61B 5/024* (2006.01)
*A61B 5/0531* (2021.01)
*A61B 5/282* (2021.01)
(Continued)

(52) U.S. Cl.
CPC ............ *A61B 5/721* (2013.01); *A61B 5/0205* (2013.01); *A61B 5/02427* (2013.01);
(Continued)

(58) Field of Classification Search
CPC ............. A61B 5/0205; A61B 5/02405; A61B 5/02427; A61B 5/02438; A61B 5/04085; A61B 5/0531; A61B 5/0537; A61B 5/681; A61B 5/721; A61B 5/02–0295; A61B 5/0402–0472; H02J 7/00; G04G 21/00; G04G 21/025
See application file for complete search history.

(56) References Cited

U.S. PATENT DOCUMENTS 9,599,632 B2 3/2017 Yuen
10,321,874 B2 * 6/2019 Eom ..................... A61B 5/742
(Continued)

FOREIGN PATENT DOCUMENTS

WO 2013/132147 A2 9/2013
WO 2014/088768 A2 6/2014

OTHER PUBLICATIONS

International Search Report for PCT Patent Application No. PCT/EP2017/071428, dated May 16, 2018, 6 pgs.

*Primary Examiner* — Jonathan T Kuo
(74) *Attorney, Agent, or Firm* — FisherBroyles, LLP

(57) ABSTRACT

There is provided a wearable device for measuring cardiac activity of a user, the wearable device comprising: an optical cardiac activity sensor unit configured to be placed in contact with a measurement area and to enable cardiac activity measurement of the user to obtain a cardiac activity signal; a plurality of electrodes configured to enable bio-impedance measurement on the measurement area to obtain a bioimpedance signal; a detector unit for detecting changes in the bioimpedance signal; and a reducer unit for reducing a motion artefact effect on the cardiac activity signal based on the detected changes in the bioimpedance signal.

15 Claims, 14 Drawing Sheets

(51) Int. Cl.
  *A61B 5/0205* (2006.01)
  *A61B 5/0537* (2021.01)
  *H02J 7/00* (2006.01)
  *A61B 5/318* (2021.01)

(52) U.S. Cl.
  CPC ........ *A61B 5/02438* (2013.01); *A61B 5/0531* (2013.01); *A61B 5/0537* (2013.01); *A61B 5/282* (2021.01); *A61B 5/681* (2013.01); *A61B 5/02405* (2013.01); *A61B 5/318* (2021.01); *H02J 7/00* (2013.01)

(56) References Cited

U.S. PATENT DOCUMENTS

| | | | |
|---|---|---|---|
| 10,376,164 B2* | 8/2019 | Presura | A61B 5/02427 |
| 10,448,896 B2* | 10/2019 | Kang | A61B 5/0402 |
| 2004/0034294 A1* | 2/2004 | Kimball | A61B 5/02125 600/323 |
| 2014/0058217 A1* | 2/2014 | Giovangrandi | A61B 5/0295 600/301 |
| 2014/0278220 A1* | 9/2014 | Yuen | G01B 21/16 702/150 |
| 2015/0265217 A1* | 9/2015 | Penders | A61B 5/721 600/301 |
| 2016/0007926 A1* | 1/2016 | Kang | A61B 5/0402 600/301 |
| 2016/0113578 A1* | 4/2016 | Eom | G16H 40/67 600/547 |
| 2016/0128604 A1 | 5/2016 | Eom et al. | |
| 2016/0324433 A1 | 11/2016 | Tan et al. | |
| 2017/0086753 A1* | 3/2017 | Presura | A61B 5/02427 |
| 2017/0164884 A1* | 6/2017 | Culbert | A61B 5/0873 |
| 2019/0209028 A1* | 7/2019 | Baxi | A61B 5/00 |

\* cited by examiner

ENHANCING OPTICAL CARDIAC ACTIVITY MEASUREMENT

CROSS-REFERENCE TO RELATED APPLICATION

This application claims benefit to International Patent Application No. PCT/EP2017/071428, filed Aug. 25, 2017, which is incorporated by reference herein in its entirety.

BACKGROUND

Field

The invention relates to cardiac activity measurement. Moreover, the invention relates to reducing an effect of motion artefacts in cardiac activity signals.

Description of the Related Art

Optical cardiac activity measurement, such as measuring heart rate using a wrist device comprising an optical sensor, has become increasingly popular. At the same time, the quality of such measurements may be reduced by, for example, movement of the optical sensor with respect to body tissue. Hence, it may be beneficial to provide solutions which reduce effect of motion artefacts in cardiac activity signals.

SUMMARY

According to an aspect, there is provided a wearable device for measuring cardiac activity of a user, the wearable device comprising: an optical cardiac activity sensor unit configured to be placed in contact with a measurement area and to enable cardiac activity measurement of the user to obtain a cardiac activity signal; a plurality of electrodes configured to enable bioimpedance measurement on the measurement area to obtain a bioimpedance signal; a detector unit for detecting changes in the bioimpedance signal; and a reducer unit for reducing a motion artefact effect on the cardiac activity signal based on the detected changes in the bioimpedance signal.

According to an aspect, there is provided a method in an apparatus for measuring cardiac activity of a user, the method comprising: obtaining a cardiac activity measurement signal from an optical cardiac activity sensor unit configured to be placed against a body tissue of the user; obtaining a bioimpedance measurement signal utilizing a plurality of electrodes configured to be placed against the body tissue; detecting changes in the bioimpedance measurement signal; and reducing a motion artefact effect, caused by a movement between the optical cardiac activity sensor unit and the body tissue, on the cardiac activity measurement signal based on the detected changes in the bioimpedance measurement signal.

According to an aspect, there is provided a computer program product comprising program instructions which when loaded into an apparatus cause the apparatus to perform a method comprising: obtaining a cardiac activity measurement signal from an optical cardiac activity sensor unit configured to be placed against a body tissue of the user; obtaining a bioimpedance measurement signal utilizing a plurality of electrodes configured to be placed against the body tissue; detecting changes in the bioimpedance measurement signal; and reducing a motion artefact effect, caused by a movement between the optical cardiac activity sensor unit and the body tissue, on the cardiac activity measurement signal based on the detected changes in the bioimpedance measurement signal.

Some embodiments are defined in the dependent claims.

One or more examples of implementations are set forth in more detail in the accompanying drawings and the description below. Other features will be apparent from the description and drawings, and from the claims.

BRIEF DESCRIPTION OF THE DRAWINGS

In the following embodiments will be described in greater detail with reference to the attached drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
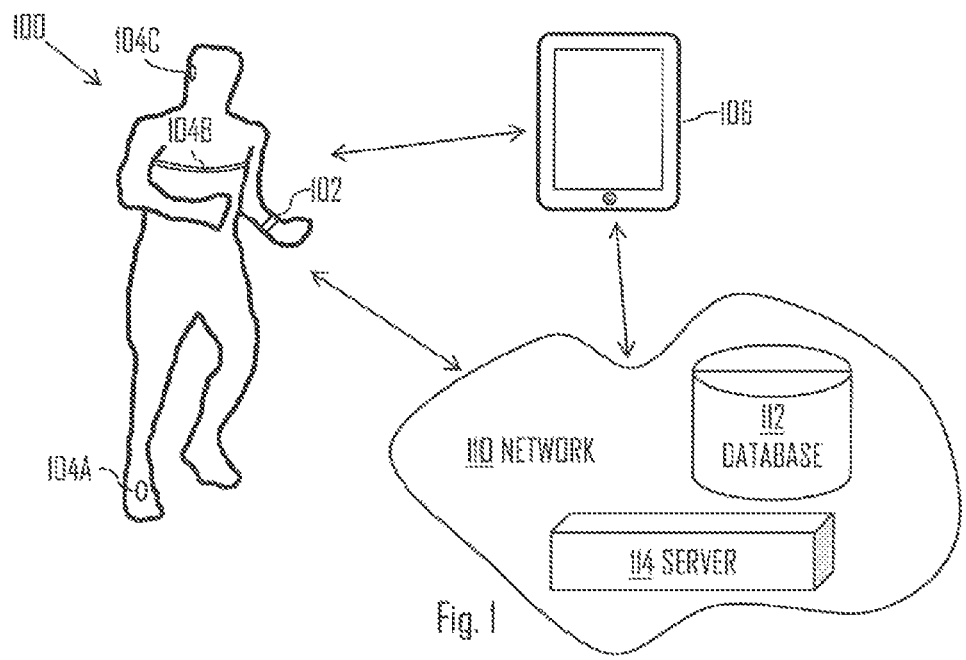
FIG. 1 illustrates a system to which embodiments of the invention may be applied.

FIG. 1 illustrates a system to which embodiments of the invention may be applied. Said system may be used to monitor physical training, activity, and/or inactivity of a user 100. Thus, the embodiments may not be limited to monitoring and/or measuring physical training of the user 100, and thus said system may be used to monitor physical activity and/or inactivity during the day and/or night (e.g. 24 hours a day). Such may be possible using one or more devices described with respect to FIG. 1 and in the embodiments below.

Referring to FIG. 1, the user 100 may wear a wearable device, such as a wrist device 102, a head sensor unit 104C, a torso sensor 104B, and/or a leg sensor 104A. In another example, the wearable device may be and/or be comprised in glasses. In another example, the wearable device is comprised or configured to be coupled with a garment or garments (or apparel). Examples of such garments may include bra(s), swimming apparel, such as swimming suit or cap, and glove(s). The garment or apparel may be worn by the user. In some embodiments, the wearable device is integrated as a part of the garment or apparel. Due to simplicity reasons, let us now describe the wearable device as being the wrist device 102. However, embodiments described in relation to wrist device 102 may be utilized by other types of wearable devices. I.e. the embodiments are not necessarily limited to wrist device or devices 102.

The wrist device 102 may be, for example, a smart watch, a smart device, sports watch, and/or an activity tracking apparatus (e.g. bracelet, arm band, wrist band, mobile phone). The wrist device 102 may be used to monitor physical activity of the user 100 by using data from internal sensor(s) comprised in the wrist device 102, data from external sensor device(s) 104A-C, and/or data from external services (e.g. training database 112). It may be possible to receive physical activity related information from a network 110, as the network may comprise, for example, physical activity-related information of the user 100 and/or some other user(s). Thus, the wrist device 102 may be used to monitor physical activity related information of the user 100 and/or the other user(s). Naturally, one or more of the external sensor device(s) 104A-C may be worn by the other user(s), and thus information received from said one or more sensor device(s) 104A-C may be monitored from the wrist device 102 by the user 100. The network 110 may comprise the training database 112 and/or the server 114. The server 114 may be configured to enable data transfer between the training database 112 and some external device, such as the wearable device. Hence, the database 112 may be used to store cardiac activity measurement data, for example.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN) and/or Near Field Communication (NFC), may also be used.

In case of communicating directly with the cellular network, the wrist device 102 may comprise similar communication capabilities as mobile devices, such as 2G, 3G, LTE, LTE-A, 4G and/or 5G communication capabilities. Thus, for example, the wrist device 102 may comprise the communication circuitry capable of operating on said technologies, a Subscriber Identification Module (SIM) and/or a memory comprising a virtual SIM configured to provide a secured identification for the wrist device 102 when operating with the cellular network. It is also pointed out that, in general, the wearable device may comprise a communication circuitry capable of cellular, Bluetooth, NFC, WLAN, and/or LAN communication.

The wrist device 102 may be used to monitor activity and/or inactivity of the user 100. Similarly, the portable electronic device 106 may be used to monitor the activity and/or inactivity of the user 100. Such may require the portable electronic device 106 to acquire physical activity-related data from the wrist device 102, some other wearable device, and/or from external sensor device(s) 104A-C. However, it may be that the portable electronic device 106 determines activity and/or inactivity of the user 100 by utilizing internal sensor(s), such as accelerometer or satellite positioning circuitry.

The wrist device 102 may comprise a cardiac activity circuitry configured to determine cardiac activity of the user 100, such as heart rate, Heart Beat Interval (HBI) and/or Heart Rate Variability (HRV), for example. The cardiac activity circuitry may comprise an optical cardiac activity sensor unit configured to measure the cardiac activity of the user 100. Example of such sensor may be a PPG (photoplethysmography) sensor. The optical cardiac activity sensor unit may detect the cardiac activity of the user 100 by optical measurement, which may comprise emitting light towards body tissue of the user 100 and measuring the bounced, reflected, scattered and/or emitted light from the body tissue of the user 100. The emitted light may alter when travelling through veins of the user 100 and the alterations may be detected by the optical cardiac activity sensor unit. By using the detected data, the wrist device 102, may determine cardiac activity of the user 100, such as heart rate for example. The optical cardiac activity sensor unit may obtain via the measurement a cardiac activity signal characterizing or carrying the cardiac activity information on the user. As understood, similar cardiac activity circuitry may be comprised in some other wearable device also.

It also needs to be noted that the cardiac activity circuitry may produce raw measurement data of the cardiac activity and/or it may process the measurement data into cardiac activity information, such as heart rate for example. The sensor(s) in the cardiac activity circuitry may comprise data processing capabilities. Also, the wrist device 102 and/or some other wearable device may comprise a processing circuitry configured to obtain the cardiac activity measurement data from the cardiac activity circuitry and to process said data into cardiac activity information, such as a cardiac activity metric characterizing the cardiac activity of the user 100. For example, the measurement data of the optical cardiac activity sensor unit may be used, by the processing circuitry, to determine heart rate, HRV and/or HBI of the user 100. Further, the raw measurement data and/or processed information may be processed by the wrist device 102 or some other wearable device, and/or transmitted to an external device, such as the portable electronic device 106.

The wrist device 102 (or more broadly, the wearable device) may comprise other types of sensor(s). Such sensor(s) may include a Laser Doppler-based blood flow sensor, a magnetic blood flow sensor, an Electromechanical Film (EMFi) pulse sensor, a temperature sensor, a pressure sensor, and/or a polarization blood flow sensor.

In an embodiment, the wearable device comprises a motion circuitry configured to measure motion induced by the user 100 to the wearable device, for example, by moving hand (if the wearable device is the wrist device). The motion circuitry may comprise one or more gyroscopes, one or more accelerometers and/or one or more magnetometers. The motion circuitry may use other motion data, such as location data of the user, to determine motion of the user 100. For example, the motion circuitry may comprise a satellite positioning circuitry, such as a global navigation satellite system (GNSS) circuitry. The GNSS circuitry may comprise, for example, a Global Positioning System (GPS) and/or a GLObal NAvigation Satellite System (GLONASS). The satellite positioning circuitry may be used for receiving satellite positioning data. The satellite positioning data may be used, by the wearable device, to determine motion and/or location of the user 100.

In an embodiment, the motion circuitry comprises at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor. Thus for example, the satellite positioning data may also be utilized in the sensor fusion.

Measuring cardiac activity of the user with the optical cardiac activity sensor unit (referred to simply as OHR), may be affected by motion artefacts. That is, motion artefacts may cause an effect on the measured cardiac activity signal. The effect may cause the information carried by the signal to be erroneous and/or incomplete. On the other hand, the OHR may not be in good contact with the body tissue (e.g. skin) of the user 100, which may cause possible problems in the measurement. Therefore, there is provided a solution to reduce the effect of motion artefacts on a cardiac activity signal measured using the OHR. The solution may enable the users to receive even more accurate cardiac activity information to help them, for example, during physical training or to plan their future training sessions.

Figure 2A:
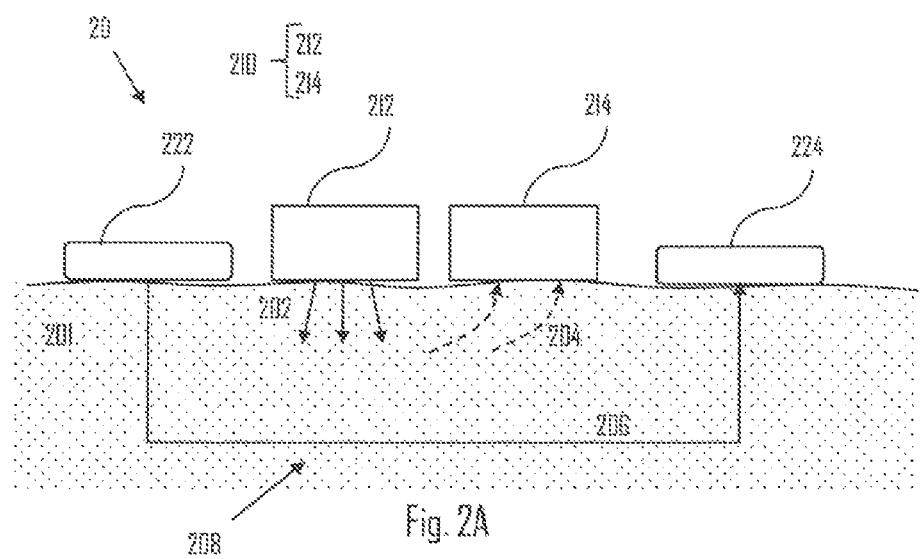
FIGS. 2A to 2F illustrate some embodiments.

FIG. 2A illustrates an arrangement 20 (could be referred to as a measuring head 20) for measuring cardiac activity of the user 100 according to an embodiment. Said arrangement 20 may be comprised in a wearable device. One example of such wearable device may be seen in FIG. 3A. Said wearable device 200 may be the wearable device discussed in relation to FIG. 1.For example, the wearable device 200 may be the wrist device 102, head sensor 104C, torso sensor 104B (e.g. physical activity measurement belt, such as a heart activity transmitter), and/or the leg sensor 104C.

Referring to FIG. 2A, the arrangement 20 comprises an optical cardiac activity sensor unit 210 configured to be placed in contact with a measurement area 208 and to enable cardiac activity measurement of the user 100 to obtain a cardiac activity signal. As explained, the cardiac activity signal may represent or carry information about cardiac activity of the user. The wearable device 200 may, based on the signal, cause transmission and/or displaying cardiac activity data to user.

Arrows 202 may indicate emitted light by the OHR 210 towards and/or into the measurement area 208. Dotted arrows 204 may indicate the light that is detected and/or detectable by the OHR 210. Based on these detections, the wearable device 200 or the OHR 210 may obtain and/or generate the cardiac activity signal.

The arrangement 20 further comprises a plurality of electrodes 222, 224 configured to enable bioimpedance measurement on the measurement area 208 to obtain a bioimpedance signal. The wearable device 200 may thus obtain the cardiac activity signal and the bioimpedance signal which are both associated with the same measurement area 208. The measurement area 208 may be comprised in a body tissue 201 (illustrated with a dotted pattern) of the user 100. Hence, both the OHR 210 and the plurality of electrodes 222, 224 may be placed in contact with the body tissue 201, and in contact with the measurement area 208.

Arrow 206 may indicate a bioimpedance measurement path between the electrodes 222, 224. The electrodes 222, 224 may be arranged and placed such that they can be used to obtain, by the wearable device 200, the bioimpedance signal representing and/or indicating bioimpedance of the measurement area. The path 206 may actually cross the emitted light 202 and/or the detected light 204 (or more generally the light path caused by the OHR 210). However, for illustration purposes it has been drawn separate from the light arrows.

The wearable device 200 may be further configured to detect (e.g. using a detector unit) changes in the bioimpedance signal and to reduce (e.g. using a reducer unit) a motion artefact effect on the cardiac activity signal based on the detected changes in the bioimpedance signal. Thus, the wearable device 200 may enhance the cardiac activity signal or form/generate a new cardiac activity signal that has less motion artefact effects compared with the originally measured signal. As shown in FIG. 2A, the body tissue 201 may form an uneven plane for the measurement arrangement 20, thus complicating the measurement even further. Hence, the enhancing the cardiac activity signal as proposed in this solution may be even more useful.

In an embodiment, diameter of the arrangement of FIG. 2A is between 1 centimeter (cm) and 4 centimeters. In an embodiment, the arrangement of FIG. 2A may have even smaller diameter than 1 cm. Diameter may refer to distance between the two outermost electrodes. In the example of FIG. 2A, this may mean distance between the electrodes 222 and 224.

Figure 2B:
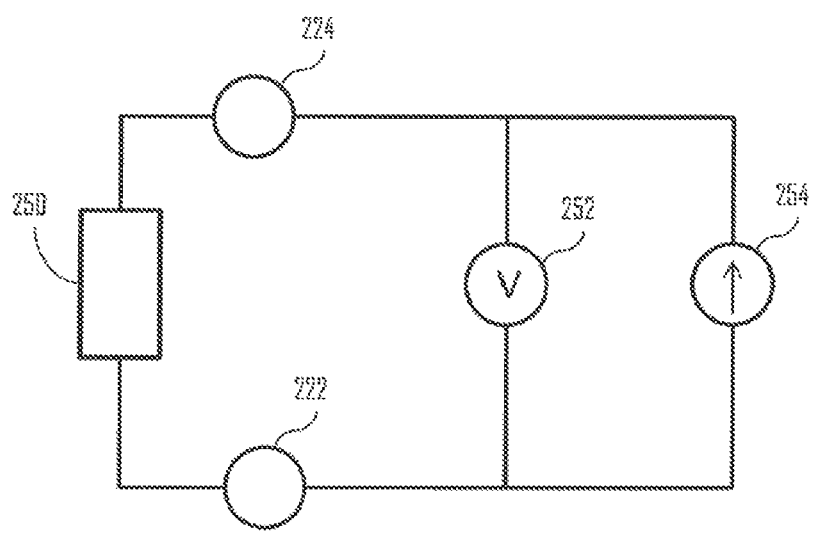

Let us first discuss how the bioimpedance measurement can be performed by looking at an embodiment of FIG. 2B illustrating a circuit diagram of bioimpedance measurement. Bioimpedance may describe electrical properties of a biological tissue. Biological tissues and cells are conductive and can be modelled as resistive and/or capacitive elements. When current flows through biological tissue of the user 100, the corresponding bioimpedance can be measured by the electrodes 222, 224 (or some other electrodes) contacting the body tissue (e.g. skin) of the user 100. Bioimpedance measurement, in general, can be used as means to measure, for example, body composition of the user. However, in the context of the present solution, it may provide some valuable information about the motion artefacts associated with the OHR 210 measurement.

Referring to FIG. 2B, the electrodes 222, 224 may be arranged to measure impedance of an object 250. In the context of the presented solution, the object 250 may refer to the measurement area 208. I.e. the electrodes may be arranged to measure bioimpedance from or of the measurement area 208. The measurement area 208 may be part of a human body or situated in a part of a human body (e.g. arm, wrist, leg, ankle, ear, head, forehead, chest). Hence, the bioimpedance measurement. The wearable device 200 may further comprise a voltage meter 252 (or similar voltage measurement means) coupled in parallel with a current source 254 (or similar electric current providing means).

As discussed, the current source 254 (e.g. alternative current (AC) source) may be connected in between the plurality of electrodes 222, 224 (e.g. the two electrodes). Additionally, one or more biasing resistors (no shown in FIG. 2B) may be coupled in between the plurality of electrodes 222, 224 (or in other words in parallel with the AC source 254). An AC coupling capacitor (not shown in FIG. 2B) may be coupled in between one of the electrodes 222, 224 and the AC source 254. Another AC coupling capacitor (not shown in FIG. 2B) may be coupled in between another one of the electrodes 222, 224 and the AC source 254. Said capacitors may be used to remove direct current (DC) component from the AC source. The capacitors and/or the resistor(s) may be used to filter out low frequency noise from the bioimpedance signal. In general, the bioimpedance of the measurement area 208 may be obtained by the wearable device by dividing the measured voltage (e.g. voltage meter 252) with the known current (e.g. current source 254). In case at least one of the electrodes 222, 224 (e.g. an electrode pair selected among a plurality of electrodes) is not in contact (or not sufficiently in contact) with the body tissue of the user 100, the impedance signal may be based on measuring the impedance of the one or more biasing resistors (in case such resistors are used). The resistance of said biasing resistors can be selected to such that the non-contact or insufficient contact situation may be detected by the wearable device 200. That is, as the resistance of said biasing resistor may be known, the measured impedance signal may indicate certain predictable or known values. Furthermore, if the resistance of the biasing resistors is configured to be substantially higher than the largest possible impedance of the measurement area 208, the non-contact or insufficient contact situation may be detected.

In an embodiment, the frequency of the AC signal is lower than 100 kHz (e.g. 1-100 kHz). In one example, the frequency of the AC signal may be 0-10 kHz. Different frequencies or frequency areas may be used to reveal different parameters of the user.

Using the shown arrangement of FIG. 2B, the impedance of the object 250 may be measured. It needs to be noted that the shown arrangement may be one suitable way to perform the measurement. Hence, other suitable measurement arrangements for measuring bioimpedance of the measurement area 208 may be used.

Figure 2C:
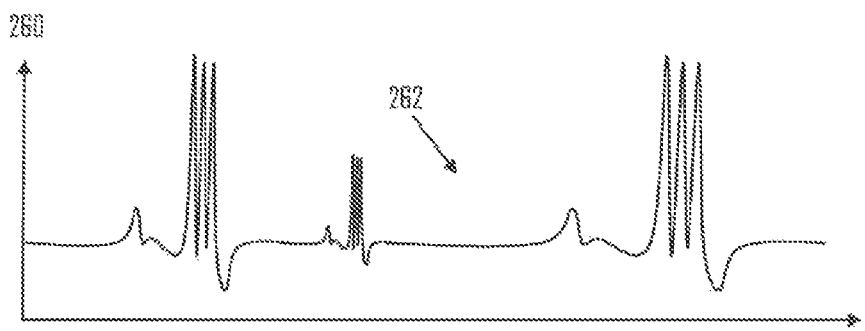
Figure 2D:
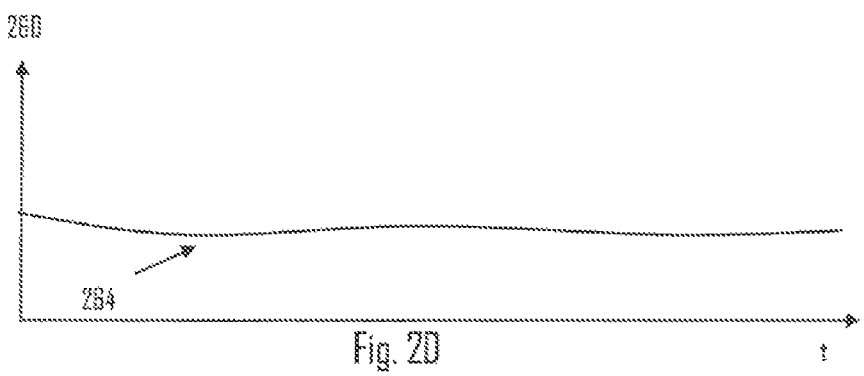

FIGS. 2C and 2D illustrate some examples of a bioimpedance signal acquired using the plurality of electrodes 222, 224 from the measurement area 208. At least two electrodes at a time are used, by the wearable device 200, to measure the bioimpedance signal. Referring to FIG. 2C and 2D, bioimpedance 260 may indicated as a function of time t. Bioimpedance signal 262 of FIG. 2C may indicate bioimpedance signal in case the contact of the OHR 210 with the body tissue of the user 100 is not sufficient or not good. For example, wrist strap of the wrist device 102 may be kept too loose, and thus the signal 262 indicates greater variation compared with the bioimpedance signal 264 representing a case where the strap is kept tighter.

In an embodiment, the wearable device 200 is configured to measure contact of the OHR 210 with the body tissue based on the bioimpedance signal (e.g. 262, 264). Based on the measuring, the wearable device 200 may be configured to output a control signal. For example, the wearable device 200 may be configured to output the control signal in case the OHR 210 is not in contact with the body tissue. The control signal may cause output of a visual (e.g. via display), haptic (e.g. via vibration element) and/or sound notification (e.g. via speaker) to the user 100. Alternatively or additionally, the control signal may be transmitted, by the wearable device, to an external device (e.g. portable device 106). For example, the control signal may cause output of a notification via said external device. The measuring of contact of the OHR 210 may be performed alternatively or additionally to the reducing the effect of motion artefacts on the cardiac activity signal. In some instances it may suffice that the user is indicated that the contact of the OHR 210 is good or not good. However, in some instances this may be performed together with enhancing the cardiac activity signal by removing or reducing the motion artefact effect. The determination whether the OHR 210 is in good or sufficient contact with the body tissue may be based on comparing the bioimpedance signal against one or more thresholds. For example, if the bioimpedance signal is between certain thresholds, the contact may be determined, by the wearable device 200, to be good, and bad if the signal is not within said thresholds. However, in general, the wearable device 200 may acquire the bioimpedance signals via the electrodes 222, 224, and cause the output of the control signal in case the bioimpedance signal indicates a condition indicating insufficient body tissue contact by the OHR 210. Such condition may be, for example, that the wearable device 200 may not be able to output a cardiac activity data of the user 100 (such as heart rate, HRV and/or HBI). Consequently, the control signal may be outputted by the wearable device 200.

Figure 2E:
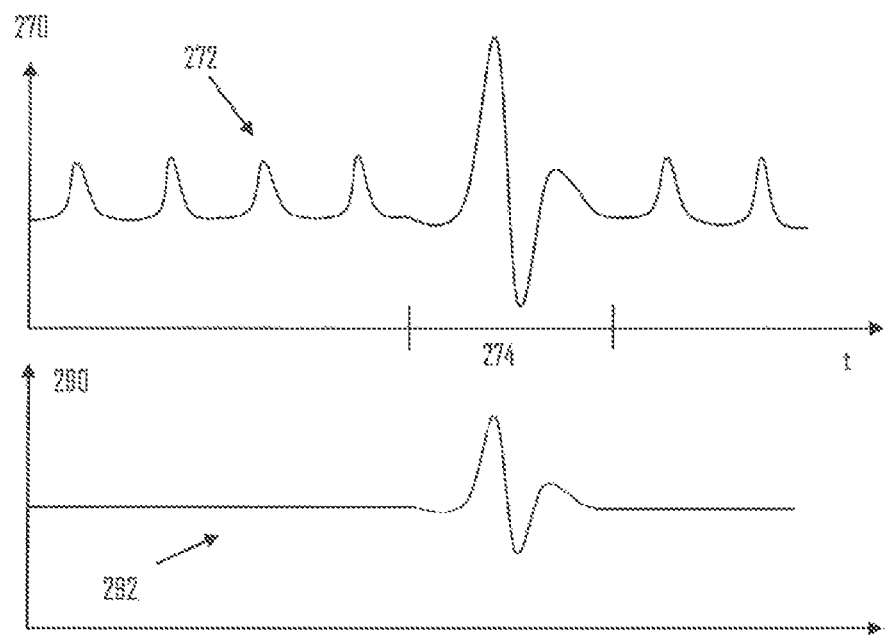
Figure 2F:
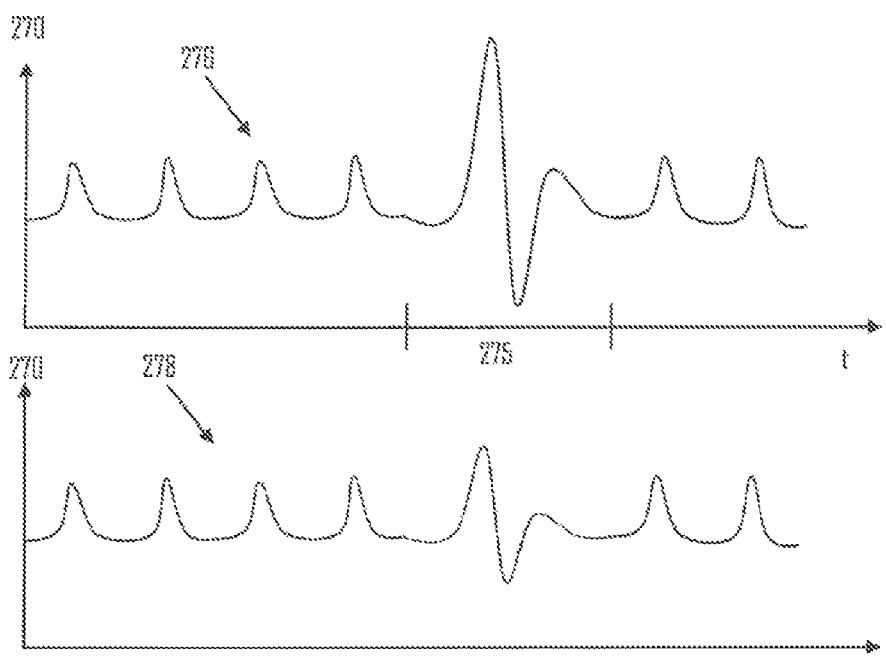

Let us then look at FIGS. 2E and 2F illustrating some examples of bioimpedance signal and cardiac activity signal(s). Referring to FIG. 2E, as said the cardiac activity signal 272, indicating cardiac activity 270 as a function of time t, may comprise some variations caused by motion artefacts. For example, at time period 274, the cardiac activity signal 272 seems to first have a pulse with higher amplitude and then the signal drops well below average level (or DC level). Looking at bioimpedance signal 292 (signals 272, 292 may be time synchronized with each other) indicating bioimpedance 290, during the same period 274 similar observation may be made. It needs to be noted that the similarity of the pattern of the signals 272 and 292 during period 274 may as well be a coincidence. However, it may also be that such observation may be made depending on the motion artefact. Now, by processing the signals 272, 292 in a certain manner, the effect of the motion artefacts on the cardiac activity signal 292, during period 274, may be reduced based on the bioimpedance signal 292. There are several ways to perform the reduction.

In an embodiment, the wearable device 200 is configured to scale the cardiac activity signal and/or the bioimpedance signal, wherein the reducing the motion artefact effect on the cardiac activity signal is further based on performing, by the wearable device, a division operation, a subtraction operation and/or an adding operation between the cardiac activity signal and the bioimpedance signal. The division, subtracting and/or adding may be performed in time domain and/or in frequency domain. In the example of FIG. 2E, the bioimpedance signal 292 may be scaled such that an average of the signal during a certain time period substantially equals to an average of the cardiac activity signal 272. Then the bioimpedance signal 292 may be subtracted from the cardiac activity signal 272, thus reducing the motion artefact effect on the cardiac activity signal 272.

In an embodiment, the wearable device 200 is configured to control (e.g. reduce, increase or repair) phase of the measured bioimpedance signal 292 and/or the cardiac activity signal 272 before reducing the motion artefact effect on the cardiac activity signal 272 (e.g. by processing the cardiac activity signal 272 based on the bioimpedance signal 292 to obtain an enhanced cardiac activity signal).

In an embodiment, the wearable device 200 is configured to determine a correlation factor between the bioimpedance signal (e.g. signal 292) and the cardiac activity signal (e.g. signal 272). In case the correlation factor indicates a correlation between the two signals exceeding a certain threshold, the wearable device 200 may trigger the motion artefact compensating. That is, for example, before proceeding to step 540 of FIG. 5, the wearable device 200 may determine whether the correlation exceeds the threshold. If the correlation does not exceed the threshold, the wearable device may not perform step 540 of FIG. 5. So, it may be useful to determine whether there is enough correlation between the two signals before trying to reduce the motion artefact effects. The correlation factor may be determined in time domain and/or frequency domain. It may also be possible that the signals (e.g. 272, 292) are filtered before determining the correlation factor. In general, there are multiple ways to do the reduction of the effect of the motion artefacts on the cardiac activity signal, such as on the signal 272, based on the measured bioimpedance signal, such as the signal 292. In the context of the present solution, the effect of the motion artefacts may cause the cardiac activity signal to comprise errors during period(s) where cardiac activity data or information (e.g. heart rate, HRV, HBI) may not be derivable. Such effects may be caused by, for example, movement between the OHR 210 and the body tissue of the user 100. For example, the OHR 210 may move with respect to the body tissue, and thus the signal obtained via the measurement may cause errors. Such movement may occur, for example, if the OHR 210 is not attached firmly enough against the body tissue. Another example, is that body tissue deformation(s) and/or change in body tissue characteristics may cause the described motion artefact effect. That is, if the user 100 squeezes his hand or fingers into a fist, such deformations may occur at the measurement area 208, which may be situated at the wrist area of the user 100. The OHR 210 may move with respect to the measurement area 208 along the skin that is being deformed. Hence, the describe effects may be caused by multiple different things, such as body tissue deformation and/or movement of the OHR 210 with respect to the body tissue.

Figure 3A:
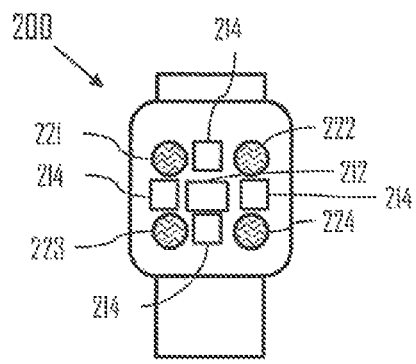
FIGS. 3A to 3C illustrate some embodiments.
Figure 3B:
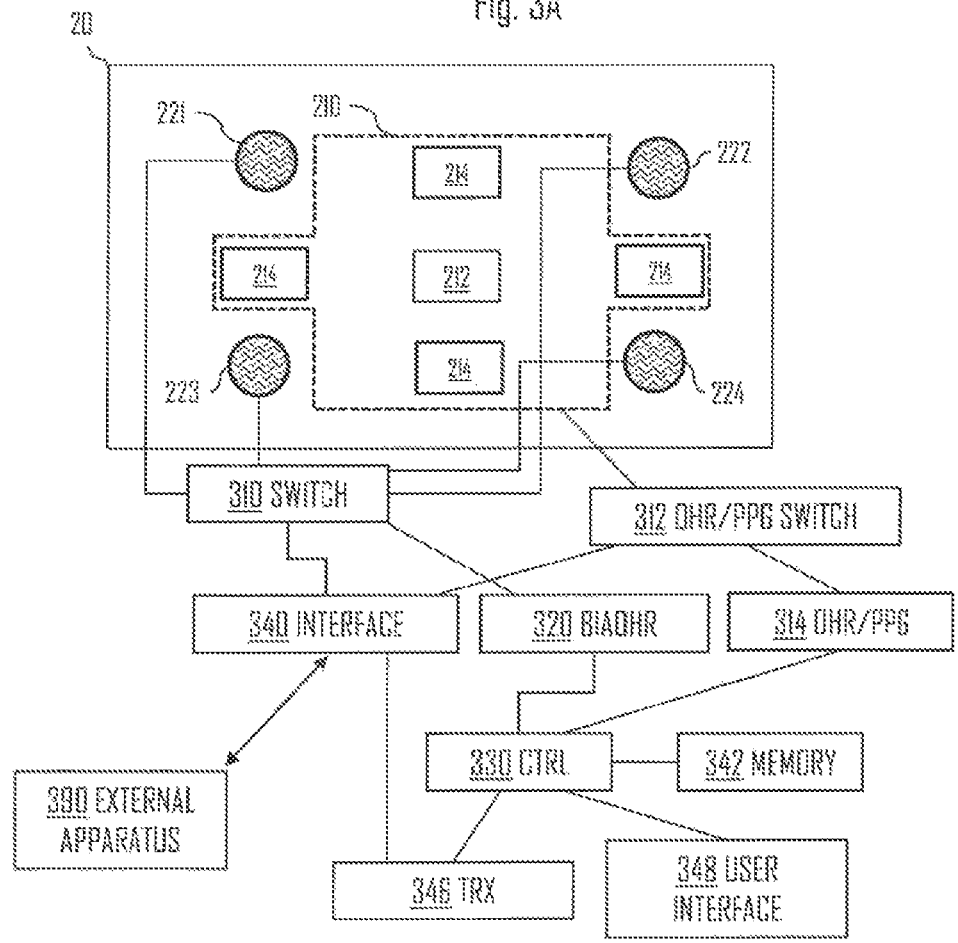

Before discussing FIG. 2F in more detail, let us look closer on FIGS. 3A and 3B illustrating the wearable device 200 according to some embodiments. Referring to FIG. 3A, the wearable device 200, such as the wrist device 102, comprises the plurality of electrodes 221-224. The plurality may comprise two or more electrodes. In the example of FIG. 3A, there are four electrodes 221-224. In some instances, the plurality of electrodes 221-224 may be referred to as bottom electrodes, as they may be situated at the bottom face or side of the wearable device 200. The electrodes 221-224 may comprise bioimpedance electrodes, electrocardiography (ECG) electrodes, and/or galvanic skin response (GSR) electrodes, for example.

In an embodiment, the wearable device 200 comprises the OHR 210 comprising a plurality of light emitting elements (LEEs) 212 and/or a plurality of light detectors 214 (e.g. photodiodes (i.e. configured for cardiac activity measurement) and/or matrix detectors). In one example, the wearable device 200 comprises one LEE 212 and four light detectors 214. Each LEE 212 may comprise one or more Light Emitting Diodes (LEDs), for example. The LEDs may be of same or different color. Different colors may comprise green (about 525 nm), red (about 630 nm), yellow (about 590 nm), and blue (about 470 nm), for example. Thus, in an embodiment, the OHR 210 may be multicolor OHR configured to use a plurality of different light wavelengths to perform the optical cardiac activity measurement.

With respect to using a plurality of different colors (i.e. different wavelengths) it is noted that the detected motion errors may be different for different wavelengths. Hence, the correlation between a cardiac activity signal and the bioimpedance signal may be different depending on the used color. For example, the bioimpedance signal may correlate better with a cardiac activity signal obtained using red color compared with a cardiac activity signal obtained using green color. Hence, the wearable device 200 may be configured to determine respectively the correlation between the bioimpedance signal and a plurality of cardiac activity signals obtained using different colors. The wearable device 200 may further be configured to select the cardiac activity signal with highest correlation with the bioimpedance signal based on the determined correlation. The selected cardiac activity signal may further be processed as described herein after and/or above to reduce the motion artefact effect on the selected signal. Similar process may be used to select a cardiac activity signal amongst a plurality of different cardiac activity signals obtained from different locations.

It may be possible to utilize different frequencies in the bioimpedance measurement (e.g. see source 254 of FIGS. 2B) to obtain as relevant biompedance signal as possible. That is, different AC frequencies may correlate better with different colors. For example, for a first color based OHR 210 measurement, the bioimpedance measurement may be configured to be performed using a first frequency, and for a second color based OHR 210 measurement, the bioimpedance measurement may be configured to be performed using a second frequency, wherein said frequencies or frequency areas are different and/or do not overlap with each other. Hence, in general, the wearable device 200 may be configured to perform bioimpedance measurement on at least two different frequencies. Each frequency may be associated with a certain selected wavelength used in OHR 210 measurement. For example, bioimpedance measurement between electrodes 221 and 222 may be performed using a first frequency and a bioimpedance measurement between electrodes 221 and 223 may be performed using a second frequency. Similar logic may be used with other electrode pairs formed from the group of electrodes 221-224 and/or electrodes 382, 384.

In an embodiment, the optical cardiac activity sensor unit (i.e. the OHR 210) comprises at least one light emitting element 212 and at least one light detector 214, wherein at least one of said at least one light emitting element 212 and said at least one light detector 214 is positioned partially or fully between first and second electrodes of the plurality of electrodes 221-224. For example, the LEE 212 may be situated between the electrodes 221 and 224, in the example of FIG. 3A. For example, the light detector 212 may be situated between the electrodes 221 and 223, in the example of FIG. 3A. However, in some cases both the LEE 212 and the detector 214 may situated between the same electrodes. Such arrangement may enable the electrodes, e.g. 221, 223, to measure bioimpedance on the propagation route of the light emitted by the LEE(s) 212 and detected by the light detector(s) 214. Hence, the changes in the bioimpedance signal may reveal effect of motion artefacts on the propagation route(s) of light between source(s) and detector(s). By forming different pairs from the plurality of electrodes 221-224, the wearable device 200 may measure bioimpedance signal(s) from plurality of different measurement areas. Such measurement area or areas (e.g. area 208) may refer to area(s) through which a light beam is transmitted by the OHR 210.

Referring to FIG. 3B, the plurality of electrodes 221-224 may be electrically connected (e.g. galvanic connection) to a switch 310 or switches of the wearable device 200. For simplicity reasons, the solution is described using only one switch 310, but more than one may still be used. The switch 310 may be used, by the wearable device 200, to select at least two electrodes (e.g. two) at a time from the plurality of electrodes 221-224 to perform the bioimpedance measurement. Hence, for example, a first electrode pair may comprise electrodes 221 and 222, a second electrode pair may comprise electrodes 221 and 223, a third electrode pair may comprise electrodes 222 and 224, a fourth electrode pair may comprise electrodes 223 and 224, a fifth electrode pair may comprise electrodes 221 and 224, and a sixth electrode pair may comprise electrodes 222 and 223. In some instances, at least one of the plurality of electrodes may be used a grounding electrode in addition to the pair used in the bioimpedance measurement. For example, this may reduce errors in the measurement caused by static electricity. The bioimpedance measurements by the plurality of electrodes 221-224 may thus be time interleaved or simultaneous. Thus, one or more bioimpedance signals may be obtained by the wearable device 200. For example, a first bioimpedance signal may be associated with a first measurement area and a second bioimpedance signal may be associated with a second measurement area. The first measurement area may be subject to optical cardiac activity measurement by a first OHR sub-unit and the second measurement area may be subject to optical cardiac activity measurement by a second OHR sub-unit, wherein each sub-unit comprises one or more LEEs 212 and/or one or more detectors 214. Hence, the different cardiac activity signals may be enhanced in the describe manner using associated bioimpedance signals. Furthermore, the enhanced (i.e. motion artefact effect reduced) different cardiac activity signals may further be used, by the wearable device 200, to obtain needed cardiac activity data or information.

The switch 310 may be connected to one or more circuitries of the wearable device 200, wherein said one or more circuitries may be configured to obtain the bioimpedance signal based on the measurements by the electrodes. For example, a BIAOHR circuitry 320 (sometimes referred to as cardiac activity bioimpedance measurement circuitry 320) may comprise the voltage meter 252 and/or the current source 254, or may be at least connected to said element 252 to obtain the bioimpedance signal. The wearable device 200 may comprise the BIAOHR circuitry 320.

According to an aspect, the wearable device 200 comprises the arrangement 20 (or measurement head 20) comprising the OHR 210 and the electrodes 221-224. The wearable device 200 may further comprise a casing enclosing one or more of elements 310, 312, 314, 320, 330, 340, 342, 346, 348, 390.

In an embodiment, the wearable device 200 comprises an optical cardiac activity switch 312 (in short OHR or PPG switch). Said switch may be connected to the OHR 210 similarly as the electrodes are connected to the switch 310. Hence, the switch 312 may be used to control the OHR 210. Controlling may comprise, for example, controlling which of the LEEs the OHR 210 are on at a time (e.g. sequencing the light emitting) or which of the detectors 214 are detecting at a time. The switch 312 may thus be connected to at least one of the elements of the OHR 210 (e.g. to all elements of the OHR 210).

In an embodiment, the switch 312 is comprised in the OHR 210.

The wearable device 200 may further comprise an optical cardiac activity circuitry 314 (can be referred to as OHR/PPG 314) electrically coupled with the switch 312 or directly with the OHR 210 in case there is no switch 312. The optical cardiac activity circuitry 314 may be configured obtain the one or more cardiac activity signals from the OHR 210. The optical cardiac activity circuitry 314 may be communicatively connected to a controller 330 (CTRL).

In an embodiment, the OHR/PPG 314 is comprised in the OHR 210. The wearable device 200 may comprise the CTRL 330 connected to the BIAOHR 320 and to the optical cardiac activity circuitry 314. Hence, the CTRL 330 may obtain the cardiac and bioimpedance signals and process them to obtain the cardiac activity signal with errors caused by the motion artefacts.

In some instances the operations of the BIAOHR 320 and/or OHR/PPG 314 are carried by the CTRL 330. Hence, the BIAOHR 320 and/or OHR/PPG 314 may not be necessary, and the CTRL 330 may thus be directly connected to the switch(es) 310, 312, to the electrodes 221-224 and to the OHR 210, depending on the implementation. In any case the CTRL 310 may be arranged such that it may receive the cardiac and bioimpedance signals, and further process them according to the embodiments described herein (i.e. obtain motion compensated/corrected optical cardiac activity signal), and to output the corrected cardiac activity signal.

The CTRL 330 may comprise at least one processor or one or more processing circuitries configured to perform the one or more operations of the wearable device 200 described above and hereinafter. For example, the CTRL 330 may be configured to cause performing, alone or together with program instructions comprised in a memory 342 of the wearable device 200, the cardiac activity measurement to obtain the cardiac activity signal and the bioimpedance measurement to obtain the bioimpedance signal.

In an embodiment, with reference to FIG. 3A, the OHR 210 comprises a first light detector and a second light detector, the first light detector situated at least partially between two electrodes (e.g. 221 and 223) of said plurality of electrodes, the second light detector situated at least partially between one of said at least two electrodes (e.g. 221 or 223) and another electrode (e.g. 222 or 224) of said plurality of electrodes.

In an embodiment, the LEE 212 is situated between two or more light detectors 214.

Still referring to FIG. 3B, the wearable device may further comprise a communication circuitry (TRX) 346 and/or a user interface 348. The user interface 348 may comprise input element for inputting information to the wearable device (e.g. controlling the wearable device) and/or output element for outputting information (e.g. audio, visual and/or haptic output elements, such as speaker, display, vibration member). The TRX 346 may be configured to enable wireless data transfer (e.g. the cardiac activity data or information), and/or wired communication via the interface 340 of the wearable device 200. Data and/or control information may be transmitted by the wearable device 200 and/or received from external device(s). Suitable communication technologies were discussed in reference to FIG. 1. One especially interesting may be Bluetooth which may be a wireless technology standard for exchanging data over short distances (using short-wavelength Ultra high frequency (UHF) radio waves in the industrial, scientific and medical (ISM) radio bands from 2.4 to 2.485 GHz). In general, short range wireless communication may be suitable for transferring the cardiac activity data to external sources. There are other options in addition or as alternatives to Bluetooth.

According to an aspect, there is provided an interface 340 electrically connected to the switch 310, and inherently to the plurality of electrodes 221-224. The interface 340 may be configured to enable charging a device (i.e. device comprising at least the plurality of electrodes 221-224, interface 340, and the switch 310) from an external source via the plurality of electrodes 221-224 and/or transferring data between said device and an external device via the plurality of electrodes 221-224. Said device may comprise a power source, such as a rechargeable battery. Said external source and/or device may depicted as external apparatus 390. For example, such apparatus 390 may comprise a power cable, external power source and/or an external electronic device (e.g. portable apparatus 106) depending on how the interface 340 is used. Said device may be the wearable device 200. Hence, the plurality of electrodes 221-224 (two or more) used to measure the bioimpedance, may be used as an interface to transfer power and/or data.

In an embodiment, the plurality of electrodes 221-224 are comprised in the interface 340.

In an embodiment, the interface 340 is a Universal Serial Bus (USB) interface.

In an embodiment, at least some of the plurality of electrodes 221-224 are used to transfer power and/or data (i.e. are comprised in the interface 340). However, all electrodes do not necessarily need to be used to both bioimpedance measurement and data/power transfer. However, using the same electrodes for both actions may provide some cost savings via material savings and/or make the device (e.g. wearable device 200) more robust as there may be less through-holes in the device. Hence, for example, there may be less apertures via which water or moist may get within the device.

In an embodiment, the interface 340 utilizes at least four electrodes of the plurality of electrodes 221-224. In an embodiment, the plurality of electrodes 221-224 comprises or consist of four electrodes. For example, USB interface may utilize four connection points, i.e. four electrodes in this case.

In an embodiment, the plurality of electrodes 221-224 (e.g. at least one of the electrodes) comprises magnetic material for magnetically coupling the device with the external apparatus 390. That is, by including magnetic material to the electrodes or to at least one of them may enable the connection between the external apparatus 390 and the interface 340 to be more stable. For example, a power cable and/or a data cable may then be more firmly connected to the interface. In an embodiment, the plurality of electrodes 221-224 comprises both the magnetic material and are also configured to be used a connection elements for the interface 340 to connect the device (e.g. wearable device 200) to the external apparatus 390. However, in some instances, the plurality of electrodes 221-224 are not used as electrical connection elements, but simply as magnetic connection elements. The power transfer and/or data transfer may then happen, for example, wirelessly (e.g. induction coil(s), TRX 346).

In an embodiment, the interface 340 is connected (e.g. galvanic connection) to the switch 312. Hence, the interface 340 may be used to control the operation of the switch 312.

Referring now to FIG. 2F, examples of two cardiac activity signals 276 and 278 are shown. Both signals 276, 278 may represent cardiac activity 270 as a function of time t. Thus, the wearable device 200 may be configured (or more precisely the OHR 210) measure two or more cardiac activity signals of the user 100. The different signals may be spatially separated and/or may be acquired using different wavelengths. For example, spatially separated signals may mean that the each cardiac activity signal is measured from a different measurement area or location of the user. For example, looking at FIG. 4A, light detectors 214A-214D may each measure light at a different locations. Similarly, one or more of the detectors 214A-D may measure or detect light having different wavelengths, wherein each wavelength may be processed as a cardiac activity signal. For example, a LEE 212A may transmit light having more than one wavelength (e.g. green and blue). Spatially and/or wavelength-wise separated cardiac activity signals may reveal different things. For example, the wearable device 200 may determine the cardiac activity signal based on a plurality of detected signals.

Figure 4A:
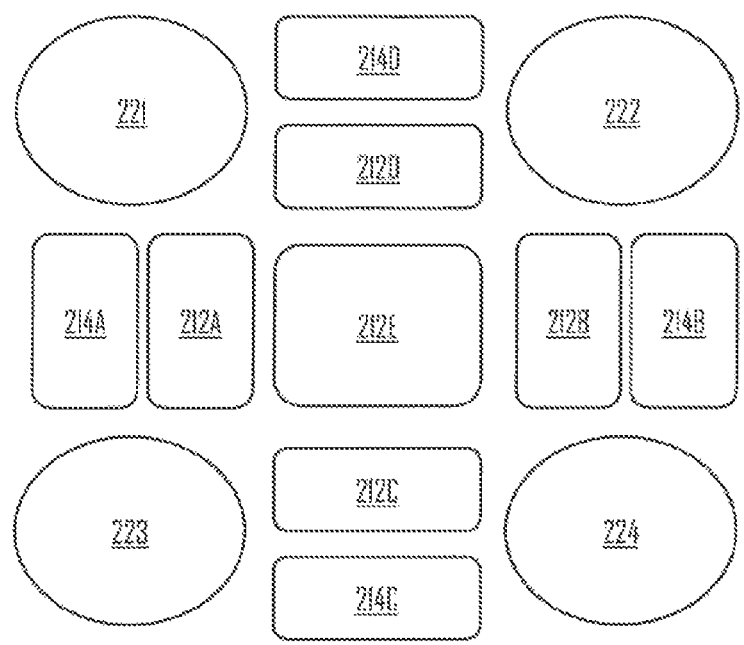
FIGS. 4A to 4H illustrate some embodiments.

Referring to FIGS. 4A and 2F as examples, in an embodiment, the optical cardiac activity sensor unit 210 comprises a first light emitting element 212A configured to emit light having a first wavelength and a second light emitting element 212B configured to emit light having a second wavelength, the optical cardiac activity sensor unit 210 configured to detect a first signal 276 caused by the emitted light having the first wavelength and a second signal 278 caused by the emitted light having the second wavelength, wherein the reducing the motion artefact effect on the cardiac activity signal is further based on performing a subtracting or addition operation between the first signal 276 and the second signal 278. For example, such operation may further reduce the motion artefact effect during the period 275 (which may be the same period as period 274). Such operation(s) may require scaling the signals 276, 278. Further, such operations may be performed in time domain and/or in frequency domain, for example.

In an embodiment, the optical cardiac activity sensor unit 210 comprises a third light emitting element 212C configured to emit light having a third wavelength, the optical cardiac activity sensor unit configured to detect a third signal caused by the emitted light having the third wavelength, the reducing the motion artefact effect on the cardiac activity signal is further based on at least halving amplitudes of the second and third signals, obtaining a sum signal of the second and third signals having the at least halved amplitudes, and performing a subtracting operation between the first signal and the obtained sum signal. That is, if there are more than two obtained signals, it may be useful to scale the signals (e.g. by adjusting DC level of the signals) before adding or subtracting the different signals with each other.

Figure 6:
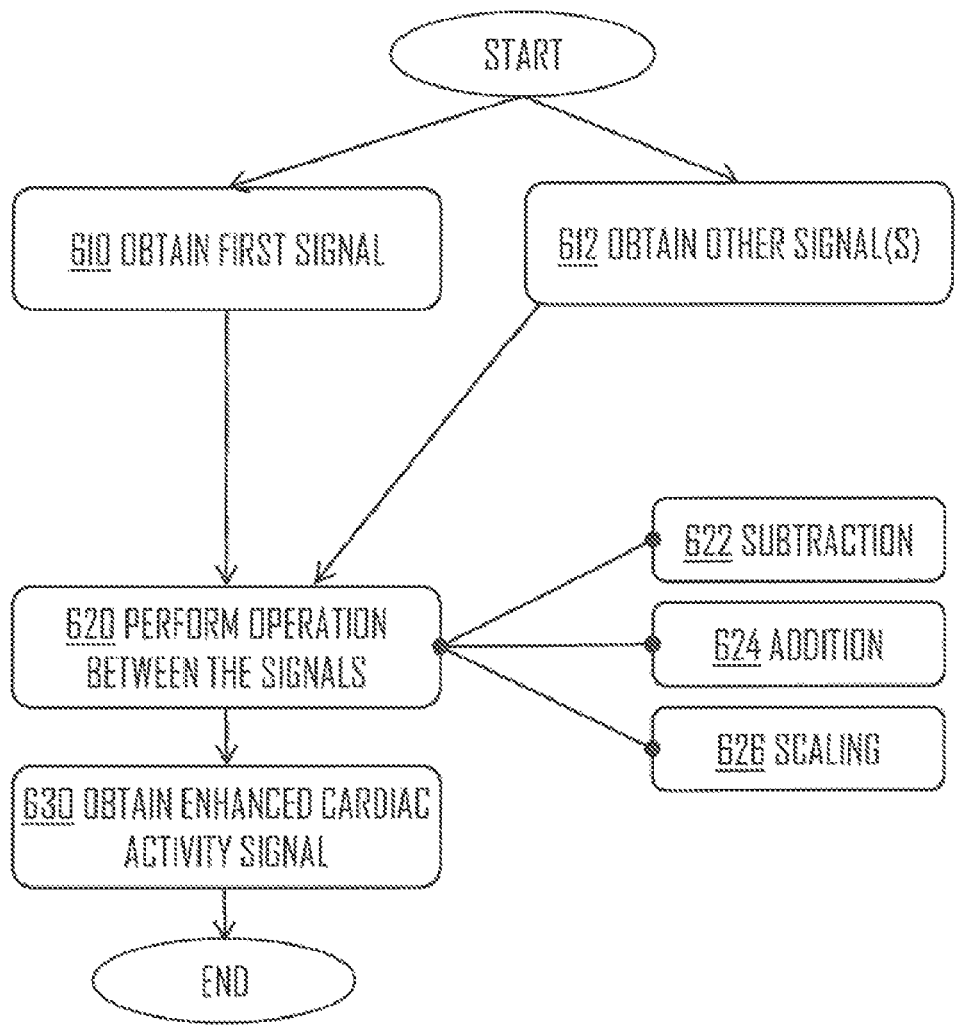

FIG. 6 illustrates a generalization of the describe embodiments of utilizing more than one cardiac activity signal. Referring to FIG. 6, the wearable device 200 may obtain the first signal (block 610) and one or more other signals (block 612). Each signal may be detected by the OHR 210, and thus used in the cardiac activity signal determination. Each signal may, at least in some embodiments, represent cardiac activity depending on the used wavelengths of emitted light. In block 620, the wearable device 200 may perform one or more operations to the signals obtained in the blocks 610 and 612. Examples of such operations include, subtraction (block 622), addition (block 624), and/or scaling (626). Based on these operations performed on the signals, the wearable device 200 may obtain the cardiac activity signal (or enhanced signal) (block 630).

Still referring to FIG. 6, in one example, the first signal is obtained from emitted substantially green light. The other signals (block 612) may be obtained from emitted substantially red and/or blue light (e.g. one is red and one is blue). The wearable device 200 may determine DC level (i.e. average) of the first signal for certain time period, and adjust the DC levels of other signal(s) according to the determined DC level of the first signal. For example, if there are two other signals in addition to the first signal, the DC levels of the two other signals may be halved. For example, if there are three other signals in addition to the first signal, the DC levels of the two other signals may be scaled to one third of the original DC level of a signal. If there is only one other signal, there may be no need to adjust the DC level. Then, sum signal of said other signals may be formed (which were scaled previously). Alternatively or additionally, the scaling (e.g. halving amplitudes and the like) may be achieved by scaling the sum signal to have same DC level as the first signal. Hence, the sum signal may be formed before scaling the other signals (obtained in block 612), and the sum signal and/or the first signal may then be scaled such that their DC level is substantially the same. Then, the sum signal may be reduced from the first signal or the first signal may be reduced from the sum signal (block 620). The result may be a signal from which DC level has been removed, and further motion errors may be removed or reduced from the signal.

This may provide even better cardiac activity signal. So, in general, the effect of the motion artefacts on the cardiac activity signal or the cardiac activity measurement may be reduced based on the bioimpedance signal or signals and/or based on a plurality of cardiac activity signals measured using different wavelengths and/or different measurement locations.

Figure 3C:
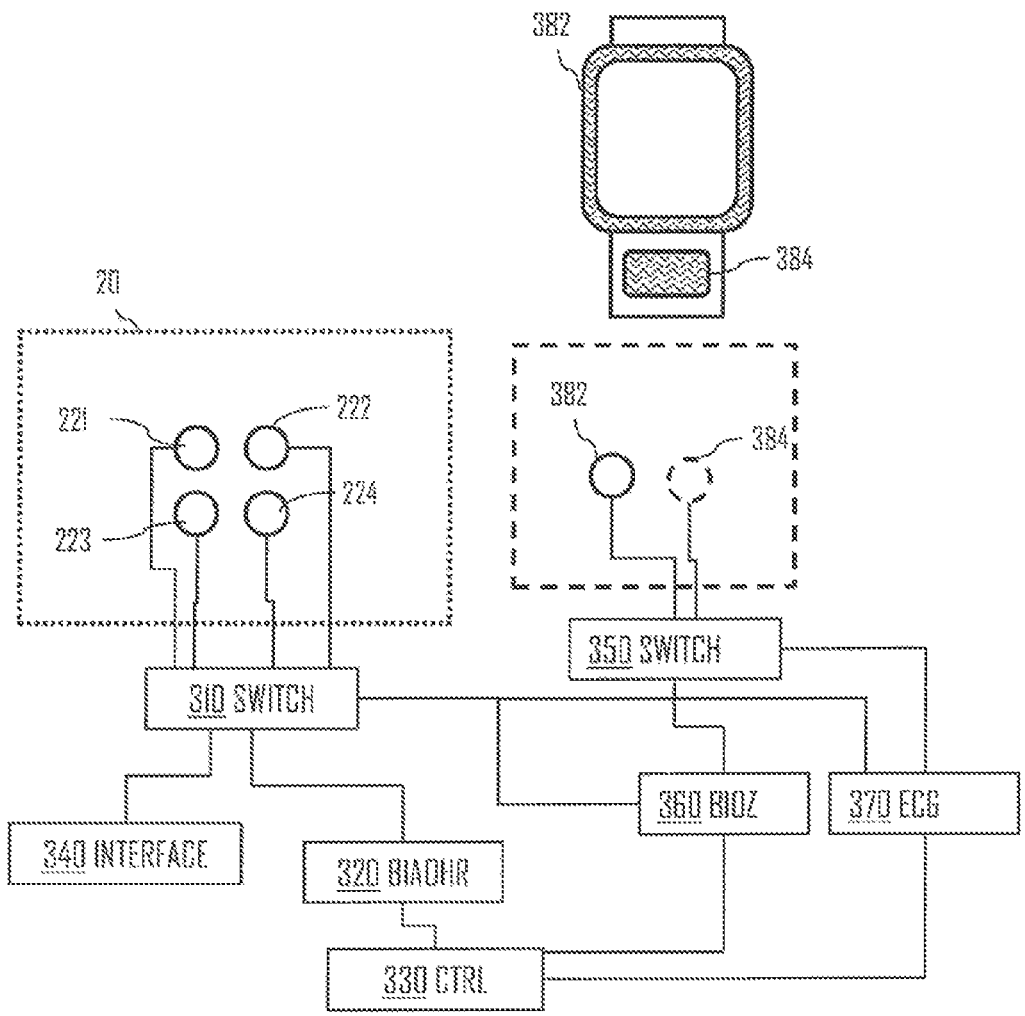

Let us then look some other aspects of the provided solution first by referring to embodiment illustrated in FIG. 3C. The wearable device 200 may further comprise at least one further electrode 382, 384 physically separate from the measurement area of the OHR 210 (e.g. measurement area 208) when said plurality of electrodes 221-224 are in contact with said measurement area. That is, said further electrode(s) 382, 384 may be arranged on a different face or side of the wearable device 200. What this may mean is that said electrode(s) 382, 384 may be configured to be used for some other measurement than measuring the bioimpedance signal of the measurement area 208. Hence, the wearable device 200 may further comprise a switch 350 for enabling said at least one further electrode 382, 384 together with at least one of said plurality of electrodes 221-224 to perform a further measurement on the user 100. Said further measurement may comprise another bioimpedance measurement, such as a measurement for determining body composition of the user 100. Additionally or alternatively, said further measurement may comprise an electrocardiography (ECG) measurement.

It first needs to be noted that although some blocks of the wearable device 200 visible in FIG. 3B are not shown in FIG. 3C, similar or the same features and/or elements may also be used in the embodiment of FIG. 3C. However, due to simplicity reasons, some aspects are not drawn into FIG. 3C.

The wearable device 200 may further comprise a BIOZ circuitry 360 connected to the at least one further electrode 382, 384 via the switch 350, and also connected to the switch 310. Connection may refer to electrical (e.g. galvanic connection). The BIOZ circuitry 360 and/or the CTRL 330 may be configured to perform the further bioimpedance measurement (e.g. body composition), and cause an output of a signal representing the measurement results. Outputting may refer to outputting the results via the user interface 348 and/or transmitting the results to an external device via the TRX 346.

The wearable device 200 may further comprise an ECG circuitry 370 connected to the at least one further electrode 382, 384 via the switch 350, and also connected to the switch 310. Connection may refer to electrical (e.g. galvanic connection). The ECG circuitry 370 and/or the CTRL 330 may be configured to perform the ECG measurement, and cause an output of a signal representing the measurement results. Outputting may refer to outputting the results via the user interface 348 and/or transmitting the results to an external device via the TRX 346.

Figure 3D:
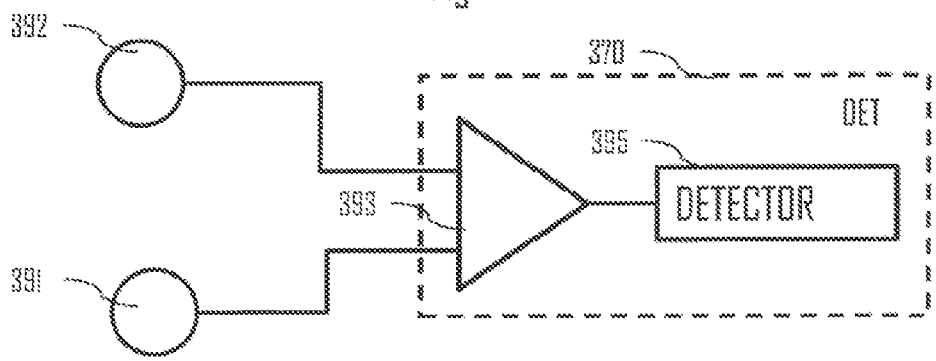
FIG. 3D illustrates an embodiment.

FIG. 3D illustrates yet another embodiment showing one example of ECG measurement arrangement. For example, the shown arrangement may comprise the ECG circuitry 370 comprising a detector 395 and a differential amplifier 393 connected to the electrodes 392, 393 via the switches 310, 350. That is, the electrode 392 may depict one of the electrodes 221-224 and the electrode 393 may depict one of the electrodes 382, 384. It is yet again noted that the use of the switches 310, 350 enables forming more than one pair from the electrodes 221-224 and electrodes 382-384.

In an embodiment, the ECG measurement arrangement is configured to measure a cardiac activity signal of a subject, the cardiac activity signal comprising ECG or a part thereof, such as P, Q, R, S, or T waves. A first signal line from a first electrode 391 may be applied to a first input of the differential amplifier 393, and a second signal line from a second electrode 392 may be applied to a second input of the differential amplifier 393. The differential amplifier 393 may operate as a front stage of the signal detection circuitry, e.g. as a first operational component counted from an input of the signal detection circuitry and carrying out pre-processing of received signals, and amplify the received biosignals differentially and apply the amplified biosignal to the detector 395 configured to detect a determined waveform in the differentially amplified biosignal, e.g. one or more of the above-mentioned P, Q, R, S, and T waves. In an embodiment, the further measurement comprises a blood pressure measurement performed by measuring a first cardiac activity signal with the OHR 210 and a second cardiac activity signal with the electrodes (e.g. electrodes 391, 392), and determining a pulse transit time (PTT) of a blood pulse(s) based on the two signals. Thus, blood pressure of the user may be determined. As described, the first and second cardiac activity signals may be measured from different locations (e.g. wrist optical heart rate measurement and finger-to-wrist ECG measurement), and thus the PTT of the blood pulse(s) may be determined. As with other measurements, the results may be displayed and/or transmitted to another device by the wearable device 200 performing said blood pressure measurement.

Using the switches 310, 350 (or simply one switch comprising functions of both switches 310, 350) may enable the selection of at least one of the electrodes 221-224 and at least one of the electrode(s) 382, 384 to perform the further measurement. In one example, the user 100 may wear the wearable device 200 in his/her wrist. Hence, the electrodes 221-224 may be brought into contact with body tissue of a first arm. The user 100 may then select to touch said further electrode(s) 382, 384. This enables electrical current to travel via a longer way or route in the user's 100 body, i.e. from one arm to another. Hence, the body composition measurement may be more reliable. Such arrangement may enable the electrodes 221-224 to be even more suitable for multiuse situations, e.g. motion artefact compensation, provide part of an interface (charging and/or data transfer), and/or enable further electrode based measurements on the user. Hence, using the additional further electrode(s) 382, 384 (e.g. only one electrode) actually may even further enhance the inventive merit of the provided solution in which the electrodes 221-224 are used.

According to an aspect, there is provided a wearable device comprising only one of said electrodes 221-224 and at least one further electrode 382, 384. Such may enable at least the body composition and/or ECG measurements.

In an embodiment, the at least one further electrode 382, 384 is comprised in a bezel of the wrist device 102. Said bezel may be a multipurpose bezel configured to be rotated between at least two positions. Each position may cause the wrist device 102 to enter a certain mode. For example, one mode may be a normal mode (e.g. training mode). For example, one of said modes may be the ECG and/or bioimpedance measurement mode. When in said ECG mode or said bioimpedance mode, the wrist device 102 may be configured to perform the ECG measurement and/or the body composition measurement. When in the normal mode, the wrist device 102 may perform the cardiac activity measurement, wherein the electrodes 221-224 may be used to reduce the motion effects. The bezel may be a part of the user interface 348, for example. In an embodiment, the at least one electrode 382, 384 is situated around a display of the wearable device 348.

Figure 7:
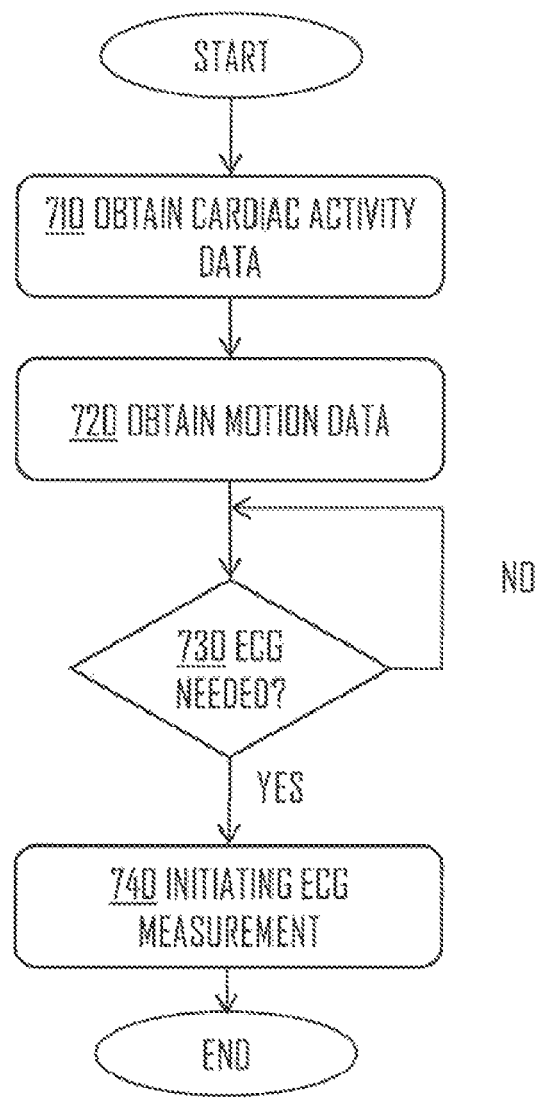

FIG. 7 illustrates a flow diagram according to yet another embodiment. Referring to FIG. 7, the wearable device 200 may obtain cardiac activity data (block 710). In an embodiment, the wearable device further obtains motion data (block 720). Blocks 710 and 720 may happen concurrently, for example. The cardiac activity data may be obtained based on the measured cardiac activity signal. The motion data may be obtained using one or more motion sensors (e.g. accelerometer, gyroscope, magnetometer), wherein the motion data may represent or characterize physical motion by the user 100.

In block 730, the wearable device 200 may determine whether or not to initiate the ECG measurement based on the obtained cardiac activity data and/or motion data. If ECG measurement is needed, said measurement may be initiated (block 740). Initiation may mean, for example, that the switch or switches 310, 350 are caused to form an electrode pair comprising one of the electrodes 221-224 and one of the electrodes 382, 384. Initiation may comprise indicating, to the user 100, that the ECG measurement is initiated or needed. The ECG measurement may then be performed accordingly. Based on the ECG measurement, the wearable device 200 may perform an action. For example, if arrhythmia is detected, it may be indicated to the user 100.

Figure 3E:
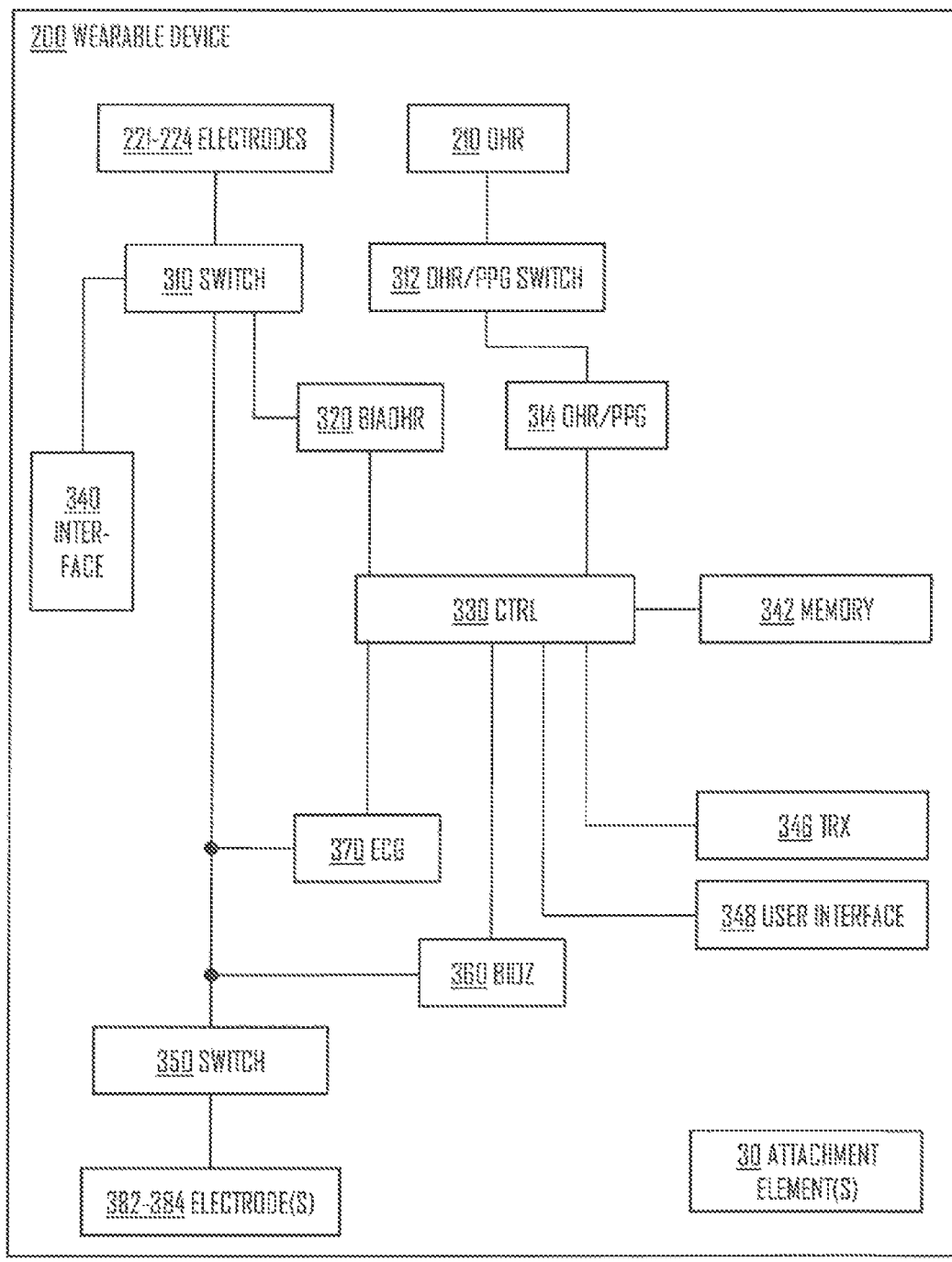
FIG. 3E illustrates an embodiment.

FIG. 3E illustrates yet another example of the wearable device 200 according to an embodiment. Referring to FIG. 3E, the wearable device 200 may further comprise an attachment element 30 configured to enable the attachment of the wearable device 200 to the user or at least the detachable placing of the OHR 210 and/or the electrodes 221-224 against the body tissue of the user. The attachment element 30 may comprise a strap and/or a garment, such as shirt, bra, or trousers. At least some of the connections between the different elements of the wearable device 200 are shown in FIG. 3E. It needs to be noted that at least in some embodiments, the OHR 210 further comprises the OHR/PPG switch 312 and/or the OHR PPG circuitry 314. The interface 340 may be connected to the CTRL 330 (although the connection is not shown in FIG. 3E). Hence, the possible data and/or power transfer via the interface 340 may be controlled by the CTRL 330, for example. In an embodiment, the attachment element 30 comprises silicone based material. In an embodiment, the wearable device 200 is detachably attachable to the attachment element 30. For example, the device 200 may be an electronics module that may be detachably attached to the element 30, the pair thus forming the wearable device 200. Let us then look closer on FIGS. 4A to 4H illustrating some embodiments. Said embodiments may relate to different layout structures for the OHR 210 and/or the plurality of electrodes 221-224. Referring to FIG. 4A which was already briefly discussed, the OHR 210 may comprise a plurality of light detectors 214A-D and plurality of LEEs 212A-E. In an embodiment, the light detector 214A is configured to mainly detect light originated from the LEE 212A. Similarly, the light detector 214B may be configured to mainly detect light originated from the LEE 212B, the light detector 214C may be configured to mainly detect light originated from the LEE 212C, and the light detector 214D may be configured to mainly detect light originated from the LEE 212D. In addition, the plurality detectors 214A-D may be configured to detect light from the LEE 212E. In an embodiment, LEEs 212A-D are configured to emit substantially blue and/or green light and LEE 212E are configured to emit substantially red and/or yellow light.

Each of the light detectors, such as detectors 214A-214D, may comprise one or more photodiodes. Similarly, each of the LEEs, such as LEEs 212A-212E, may comprise one or more LEDs or similar light source. The LEDs may be of same or different colour. As shown in FIG. 4A, the different OHR 210 elements may be situated between at least two of the electrodes 221-224. This may enable bioimpedance measurement from different OHR 210 measurement points or areas.

Figure 4B:
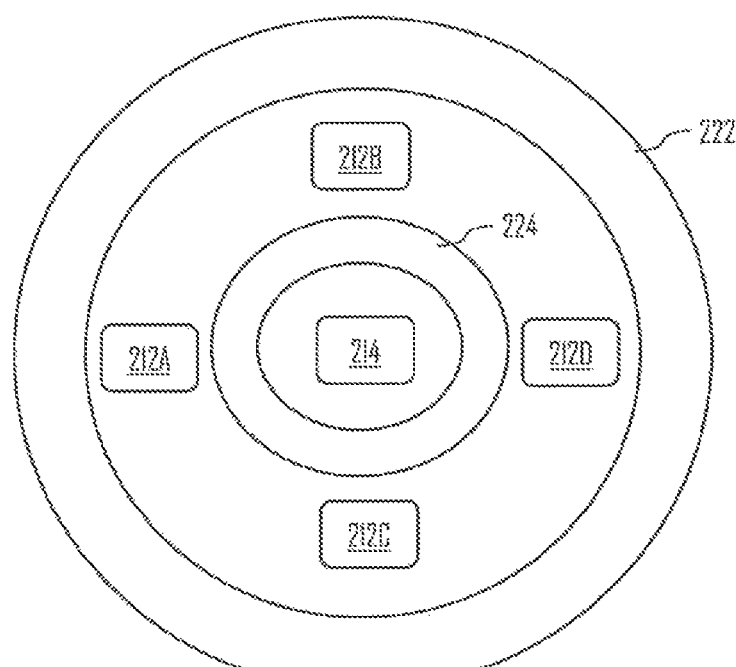

Referring to FIG. 4B, the one or more LEEs 212A-D may be arranged to be situated between a first electrode 222 and a second electrode 224. Said electrodes may be, for example, hollow electrodes, such as hollow rectangle electrodes and/or hollow circle electrodes (as shown in FIG. 4B). In an embodiment, one or more light detectors 214 are situated within the second electrode 224 being a hollow electrode. In the example of FIG. 4B, the detector 214 may be configured to detect light emitted by each of the LEEs 212A-D. The bioimpedance measurement may be performed using the two electrodes 222, 224, wherein the measurement signal is both fed and sampled from said two electrodes 222, 224.

Figure 4C:
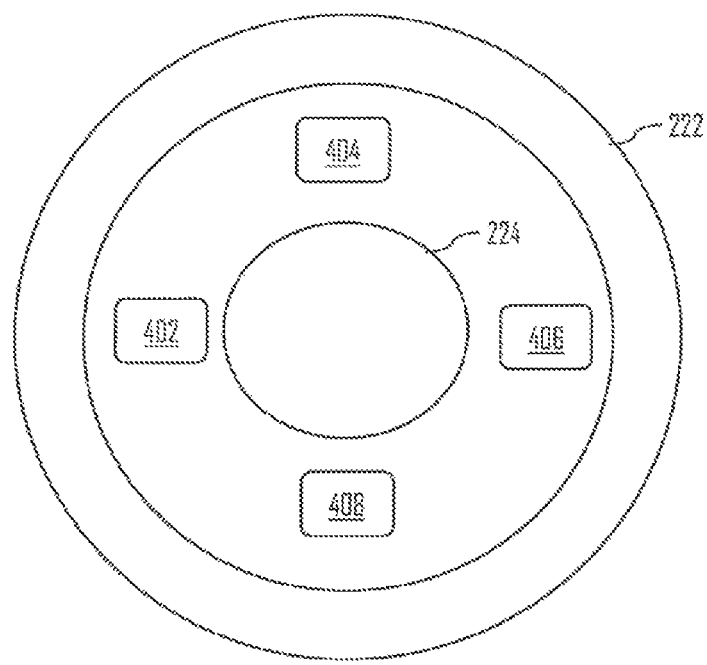

Referring to FIG. 4C, the electrodes may be similar as in FIG. 4B, but the second electrode 224 may be arranged not to be hollow. Hence, it may be shaped as a circle or a rectangle, for example. The OHR 210 elements 402-408 may be arranged between the first and second electrodes 222, 224. Each of said elements 402-408 may comprise on or more LEEs 212 and/or one or more light detectors 214.

Figure 4D:
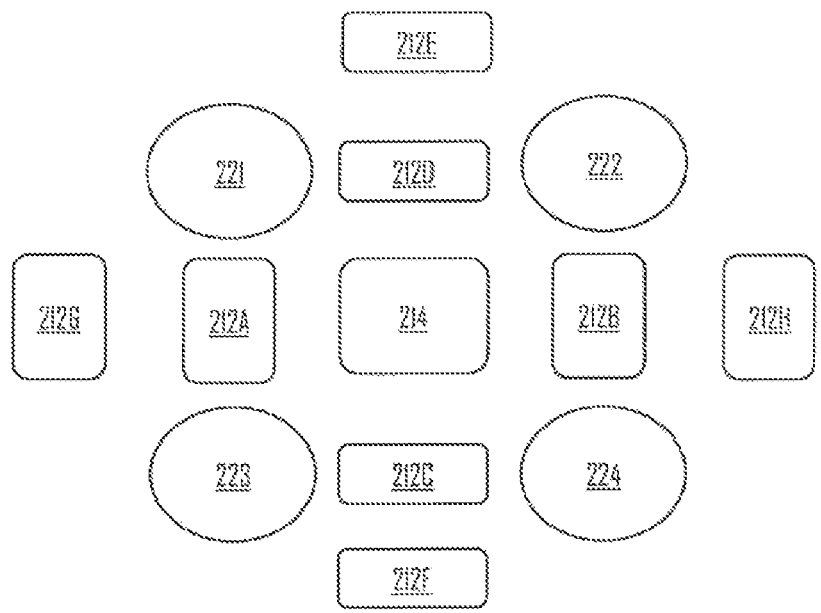

Referring to FIG. 4D, an arrangement comprising one light detector (e.g. one photodiode) 214 and a plurality of LEEs (e.g. LEDs) 212A-H is shown. As discussed earlier, the switches 310 and/or 312 may be used to select a needed electrode pair and/or needed OHR 210 elements to perform the needed measurements. For example, the switch 312 may be configured to time multiplex the burning LEEs 212A-H. That is, different LEEs may be on (i.e. emitting light) or off (not emitting light) according to the configuration by the switch 310. Hence, for example, different LEEs 212A-H may be on at different times during the measurement. In one example, LEEs 212A-H may be on according to round robin or some other similar sequence, such that after the sequence, all LEEs 212A-H have been on at least once. In some examples, more than one LEE 212A-H may be on at a time.

Figure 4E:
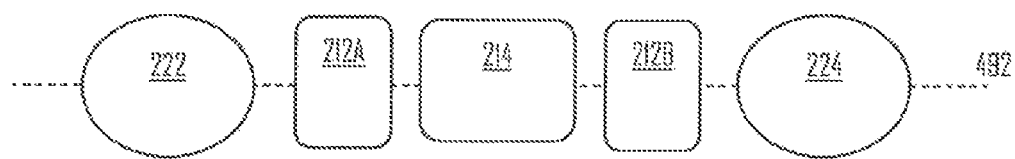
Figure 4F:
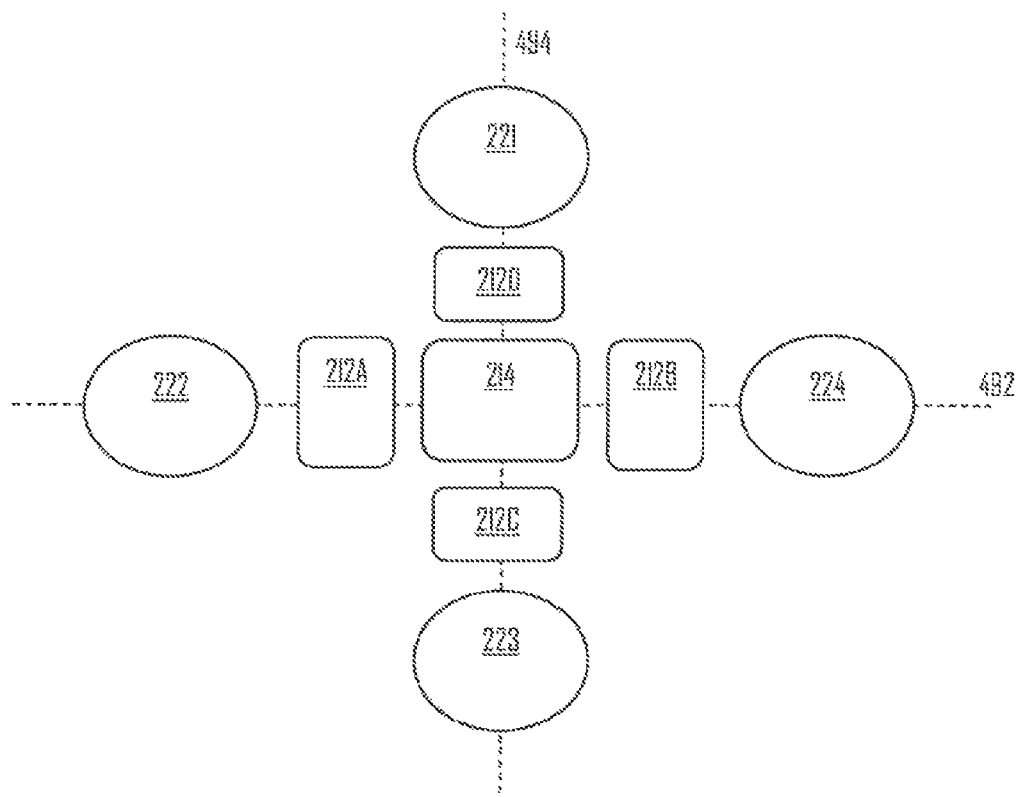

In one example, with reference to FIG. 4D, LEE 212C and 212D are configured to be on at a first time period, LEE 212A and 212B are configured to be on at a second time period, LEE 212E and 212F are configured to be on at a third time period, and LEE 212G and 212H are configured to be on at a fourth time period. Said first, second, third and fourth time periods may form the measuring sequence. For example, said periods may be consecutive. Similarly, bioimpedance electrodes 221-224 may be used to form pairs with each other. Referring to FIGS. 4E and 4F, OHR 210 symmetry axes 492, 494 are shown. That is, the symmetry axis 492 may be formed by arranging the LEEs 212A-B on two opposite sides of the light detector 214. Similarly, the symmetry axis 494 may be formed by arranging the LEEs 212C-D on two opposite sides of the light detector 214. The electrodes 221-224 may be arranged to measure bioimpedance on each of said symmetry axes 492, 494 (or simply axes). Number of said axes may be increased by including further LEEs to the arrangement. In such case, further electrodes may be needed in order to measure bioimpedance of each of said axes. One way to measure said bioimpedance may be to arrange the OHR 210 elements performing a measurement (e.g. 212C-D and 214; 212A-B and 214) between an electrode pair (e.g. 222 and 224; 221 and 223).

Figure 4H:
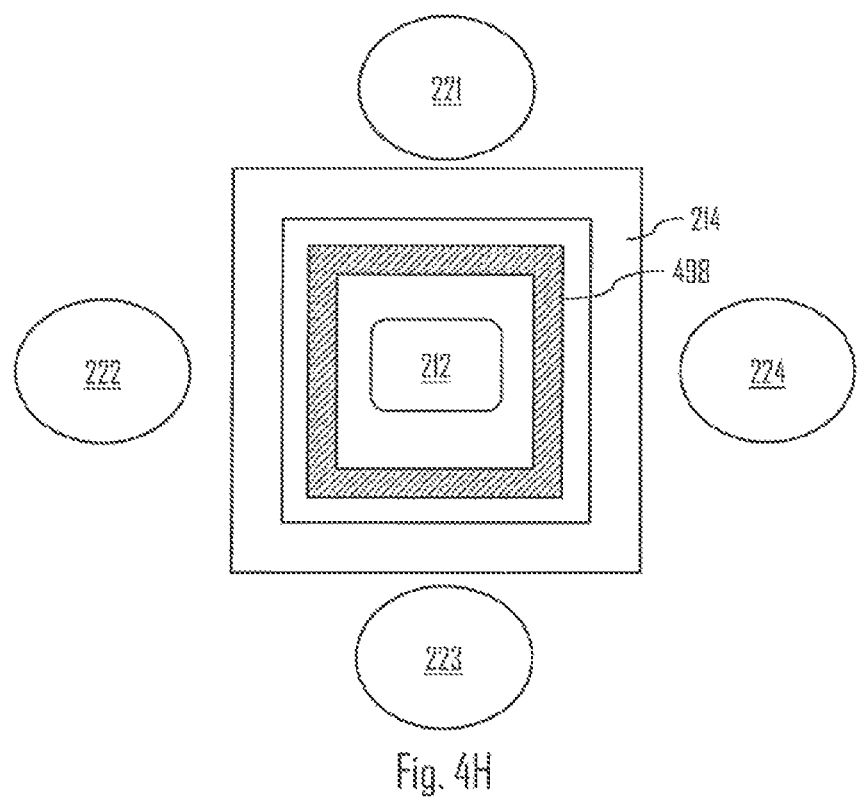

Referring to FIG. 4H, the OHR 210 may further comprise one or more light blocking elements 498. The light blocking element(s) (e.g. light wall) 498 may be arranged between the LEE(s) 212 and the light detector(s) 214, and configured to block travelling of light directly between the LEE(s) 212 and the light detector(s) 214. Hence, the detector(s) 214 may detect light that has travelled via the body tissue of the user 100, whereas leakage of light may at least substantially be reduced by the wall 498. In an embodiment, the light detector 214 is formed as a substantially hollow element, such as a hollow circle or a hollow rectangle. The light detector 214 may be formed from a plurality of photodiodes arranged in a hollow circle or hollow rectangle form, for example.

Figure 4G:
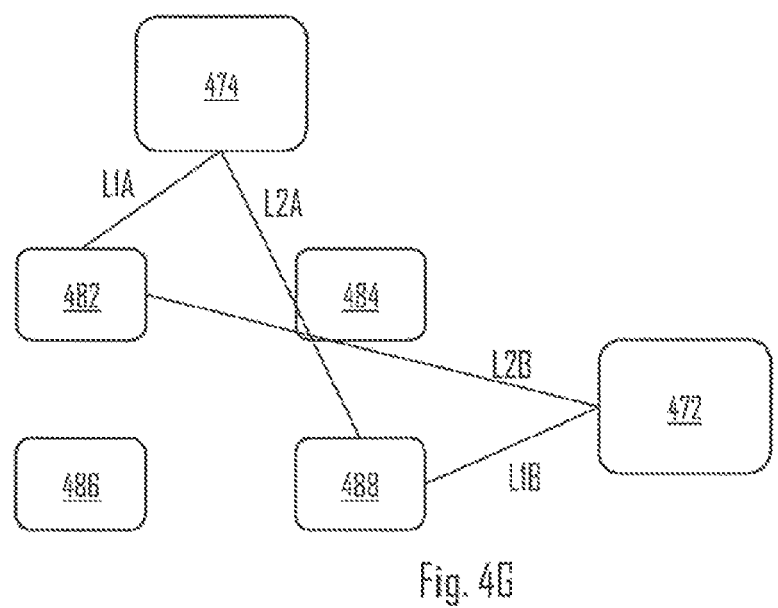

Referring to FIG. 4G, the OHR 210 comprises a first light detector 472 and a second light detector 474. These detectors may be similar to the detector 214, for example. The OHR 210 may further comprise a plurality of LEEs 482-488. The OHR 210 may further comprise the wall 498 between the LEEs and the detectors, for example. The LEEs 482-488 and the detectors 472, 474 may be arranged and dimensioned such that a distance L1A (between the first LEE 482 and the second detector 474) substantially equals to a distance L1B (between the fourth LEE 488 and the first detector 472); and a distance L2B (between the first LEE 482 and the first detector 472) substantially equals to a distance L2A (between the fourth LEE 488 and the second detector 474). Hence, the effective distance travelled by emitted light before detection by the detectors 472, 474 may be substantially same. Similar logic may apply to distances between other LEEs 484, 486 and the detectors 472, 474. In an embodiment, the LEEs 482 and 488 emit light having substantially the same wavelength (e.g. green). In an embodiment, the LEEs 484 and 486 emit light having substantially the same wavelength (e.g. yellow). In an embodiment, the light emitted by the LEEs 482 and 488 has a different wavelength compared with the light emitted by the LEEs 484 and 486. In an embodiment, the OHR 210 comprises a further LEE arranged between the LEEs 482-488. Said LEE may be arranged to emit light having a different wavelength (e.g. red) compared with light emitted by the LEEs 482-488. Said LEE may have equal distance to both detectors 472, 474, and thus the effective distance travelled by the light emitted by said LED may be the same to before the light reaches the detectors 472, 474.

The OHR 210 may further comprise one or more analog-to-digital converters (ADCs) and/or more or more amplifiers. An ADC may be electrically connected to an amplifier and the amplifier may be electrically connected to the light detector or detectors 214. The amplifier may amplify the cardiac activity signal and the ADC may convert said signal into a digital cardiac activity signal. The digital cardiac activity signal may further be processed by the CTRL 330. The processing may include obtaining cardiac activity data based on the digital cardiac activity signal. The CTRL 330 may further cause outputting said data (e.g. display via the user interface 348 or transmit via TRX 346 to an external device).

It needs to be understood that LEEs 212 and 212A-H may refer to same or similar LEEs. Similarly, detectors 214 and 214A-D may refer to same or similar light detectors.

Figure 5:
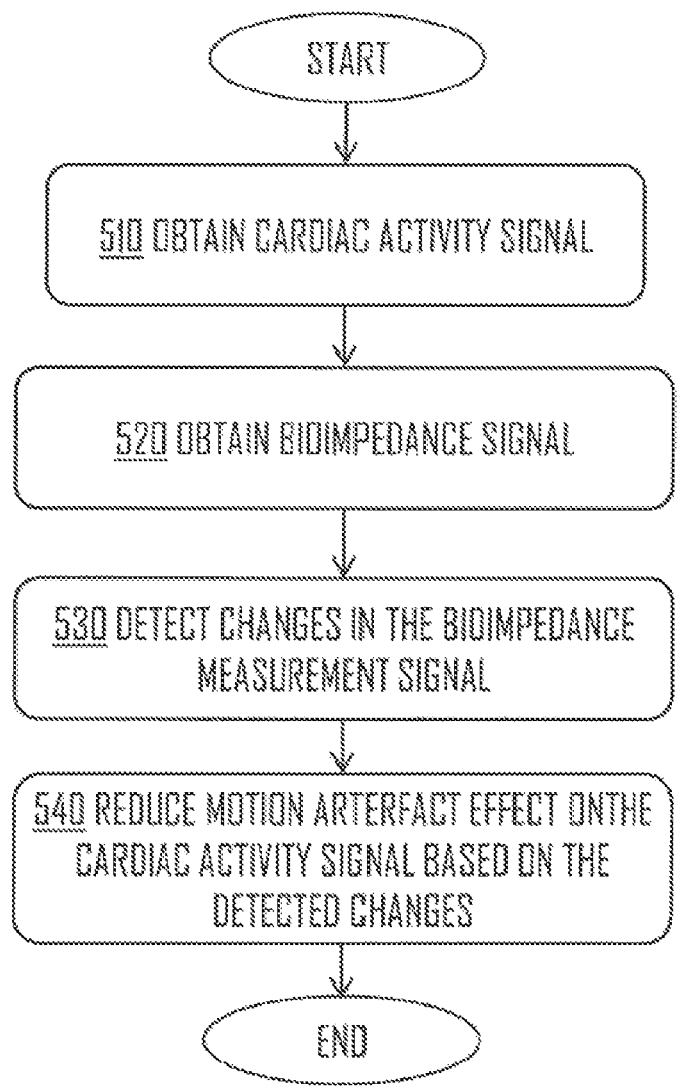
FIGS. 5, 6, 7, and 8 illustrate flow diagrams according to some embodiments.

FIG. 5 illustrates a flow diagram of a method according to an embodiment. Referring to FIG. 5, the method comprises: obtaining a cardiac activity measurement signal from an optical cardiac activity sensor unit configured to be placed against a body tissue of the user (block 510); obtaining a bioimpedance measurement signal utilizing a plurality of electrodes configured to be placed against the body tissue (block 520); detecting changes in the bioimpedance measurement signal (block 530); and reducing a motion artefact effect, caused by a movement between the optical cardiac activity sensor unit and the body tissue, on the cardiac activity measurement signal based on the detected changes in the bioimpedance measurement signal (block 540). The method may further comprise other steps described above or hereinafter (e.g. performed by the wearable device 200).

According to an aspect, there is provided a solution in which an optical cardiac activity sensor, such as the OHR 210, is configured to measure cardiac activity using sampling frequency of 10 Hz (i.e. Hertz) or below. Based on such measurement, said optical cardiac activity sensor may be used to determine breathing intervals of the user by, for example, determining variation of mean heart rate. On basis of the breathing intervals, said optical cardiac activity sensor may be used to determine sleep stages of the user, for example. For example, said optical cardiac activity sensor may comprised in a wearable device, such as the device 200, wherein said wearable device is configured to determine the breathing intervals and/or sleep stages. Further, said wearable device may be configured to transmit and/or display data indicating the breathing intervals and/or sleep stages. For example, said data may transmitted to a server for storing and further use (e.g. monitoring the user).

In an embodiment, said optical cardiac activity sensor is configured to measure cardiac activity of the user using sampling frequency of 10 Hz or below. Said optical cardiac activity sensor may be communicatively connected to a processor and/or controller of said wearable device. Said processor and/or controller may acquire cardiac activity data of the user on the basis of the measurement using sampling frequency of 10 Hz or below. Said processor and/or controller may further be configured to trigger said optical cardiac activity sensor to increase the sampling frequency to over 10 Hz. Hence, a more accurate measurement (e.g. HRV measurement) may be performed. The triggering may happen, for example, on the basis of user input, on the basis of processing the measured cardiac activity data, on the basis of measurement performed by a one or more motion sensors (e.g. accelerometer and/or gyroscope) and/or on certain time intervals (e.g. every hour or every 10 minutes). That is, the optical cardiac activity sensor may continuously measure cardiac activity to the user using the sampling rate of 10 Hz (e.g. to save battery) and increase the sampling rate (e.g. repetitively or periodically). One further example of the triggering the higher sampling frequency may be that the wearable device detects a certain sleep phase. That is, for example, the wearable device may be configured to detect that the user enters a certain sleep phase (e.g. Rapid eye movement sleep (REMS)) and to trigger the increased sampling frequency to perform some measurement (e.g. HRV). It may be beneficial to measure HRV when the user is sleeping as it may be used to determine stress of the user or quality of sleep, for example. In an embodiment, the wearable device is configured to trigger the increased sampling frequency when the user is determined to sleep. The triggering may happen periodically during sleep.

One example of the motion sensor triggered sampling rate change may be that the wearable device detects a physical activity or motion change exceeding a threshold. For example, if the user starts to run, the higher sampling rate may be triggered. In an embodiment, the triggering of the higher sampling rate may be performed in response to detecting a physical activity change (e.g. from lower activity to higher activity) associated with the user. The physical activity change may be determined on the basis of the motion sensor measurement(s) and/or optical cardiac activity measurements using the lower sampling rate. If both are used, the triggering may be performed even more accurately and timely. In an embodiment, triggering of the lower sampling rate (i.e. back to the lower sampling rate from the higher sampling rate) may be performed in response to detecting a physical activity decrease associated with the user.

Figure 8:
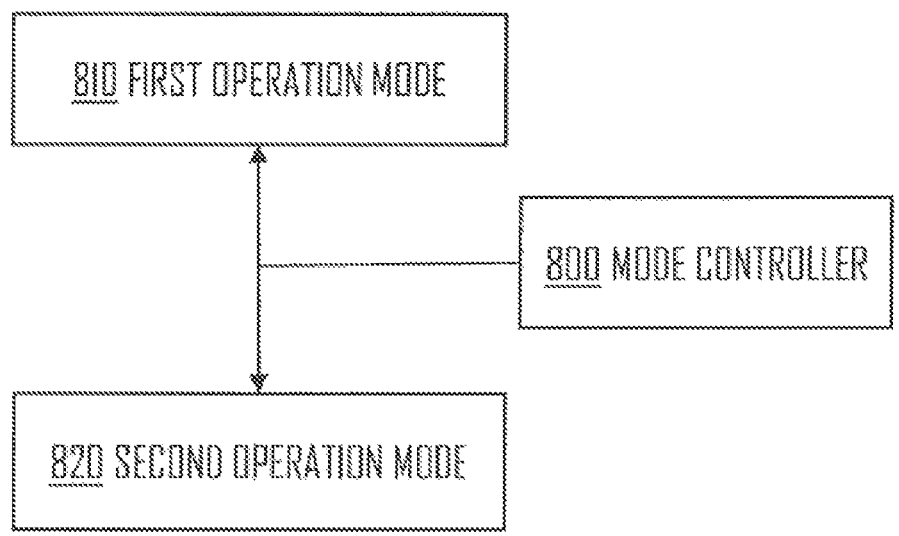

FIG. 8 illustrates an embodiment. Referring to FIG. 8, the operation modes 810, 820 may refer to operation mode of the optical cardiac activity sensor (e.g. OHR 210). In the first mode 810, the optical cardiac activity sensor may be configured to utilize the sampling frequency of 10Hz or below, whereas in the second mode 820 the sampling frequency may be higher (e.g. suitable for measuring HRV, i.e. at least over 10Hz). The optical cardiac activity sensor may be associated with a mode controller 800 configured to change the mode according to one or more conditions (e.g. user input or detecting that the user is sleeping or is in certain sleep phase). In an embodiment, the mode controller 800 comprises one or more processors. In an embodiment, the mode controller 800 is comprised in the CTRL 330 or some other part of the wearable device 200. Using a certain sampling frequency may further mean that the light emitted by the LEE(s) of the optical cardiac activity sensor is transmitted in pulses, i.e. in accordance with the sampling frequency. This may further save power.

It is further noted that using the bioimpedance measurement to cancel movement artifact effect from the cardiac activity signal may be especially purposeful and useful for the measurements performed using the lower sampling rate (i.e. 10 Hz or below). This is due to the fact that fewer samples than in normal cardiac activity measurements are received, and thus the fewer samples may be beneficial to be enhanced in the described manner.

As used in this application, the term 'circuitry' refers to all of the following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

In an embodiment, at least some of the processes described in connection with FIGS. 1 to 8 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments of FIGS. 1 to 8 or operations thereof.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments of FIGS. 1 to 8, or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 1 to 8 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium, for example. Coding of software for carrying out the embodiments as shown and described is well within the scope of a person of ordinary skill in the art. In an embodiment, a computer-readable medium comprises said computer program.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A wearable device for measuring cardiac activity of a user, the wearable device comprising:
   an optical cardiac activity sensor unit comprising a first light emitting element configured to emit light having a first wavelength, a second light emitting element configured to emit light having a second wavelength, and a third light emitting element configured to emit light having a third wavelength, the optical cardiac activity sensor unit being configured to be placed in contact with a measurement area to enable photoplethysmography measurement of the user to obtain an optically measured cardiac activity signal, the optical cardiac activity sensor unit being configured to detect a first signal caused by the emitted light having the first wavelength, a second signal caused by the emitted light having the second wavelength, and a third signal caused by the emitted light having the third wavelength;
   a plurality of electrodes configured to enable bioimpedance measurement on the measurement area to obtain a bioimpedance signal;
   a detector unit for detecting changes in the bioimpedance signal;
   a reducer unit for reducing, based on performing subtraction operation or an addition operation between the first signal, the second signal, and the third signal, a motion artefact effect on the optically measured cardiac activity signal; and
   a casing comprising the optical cardiac activity sensor unit, at least one of the plurality of electrodes, the detector unit, and the reducer unit,
   wherein the reducing the motion artefact effect on the cardiac activity signal is further based on adjusting direct current levels of the first, second, and third signals to the same direct current level before the addition operation or the subtraction operation.

2. The wearable device of claim 1, the first wavelength corresponds to green light, the second wavelength corresponds to red light, and the third wavelength corresponds to blue light.

3. The wearable device of claim 1, further comprising:
   a mode unit for changing operation mode of the optical cardiac activity sensor between a first mode and a second mode,
   wherein in the first mode the sampling rate of the optical cardiac activity sensor is configured to be equal to or below 10 Hz,
   and wherein in the second mode the sampling rate of the optical cardiac activity sensor is configured to be over 10 Hz.

4. The wearable device of claim 1, wherein the optical cardiac activity sensor unit comprises at least one light emitting element and at least one light detector, wherein at least one of said at least one light emitting element and said at least one light detector is positioned at least partially between first and second electrodes of the plurality of electrodes.

5. The wearable device of claim 4, wherein both said at least one light emitting element and said at least one light detector are positioned at least partially between said first and second electrodes.

6. The wearable device of claim 1, wherein said plurality of electrodes comprises at least three electrodes, the wearable device further comprising:
   a switch for enabling two of said at least three electrodes at a time to perform said bioimpedance measurement.

7. The wearable device of claim 6, wherein the optical cardiac activity sensor unit comprises a first light detector and a second light detector, the first light detector situated at least partially between two electrodes of said plurality of electrodes, the second light detector situated at least partially between one of said at least two electrodes and another electrode of said plurality of electrodes.

8. The wearable device of claim 1, further comprising:
   a scaling unit for scaling at least one of the cardiac activity signal and the bioimpedance signal, wherein the reducing the motion artefact effect on the cardiac activity signal is further based on performing the subtraction operation or an adding operation in time domain between the cardiac activity signal and the bioimpedance signal.

9. The wearable device of claim 1, wherein:
   the least one further electrode is physically separate from said measurement area when said plurality of electrodes are in contact with said measurement area; and
   the wearable device further comprises a switch for enabling said at least one further electrode together with at least one of said plurality of electrodes to perform a further measurement on the user.

10. The wearable device of claim 9, wherein said further measurement comprises another bioimpedance measurement for determining body composition of the user.

11. The wearable device of claim 9, wherein said further measurement comprises electrocardiography measurement.

12. The wearable device of clam 1,
   wherein the reducing the motion artefact effect on the cardiac activity signal is further based on scaling the direct current level of the second signal and the third signal to the same direct current level, obtaining a sum signal of the scaled second and third signals, and performing the subtraction operation between the first signal and the obtained sum signal, wherein the first signal and the sum signal are also scaled to the same direct current level.

13. The wearable device of claim 1, wherein the wearable device is a wrist device configured to measure physical activity of the user by obtaining cardiac activity measurement data and physical motion measurement data using one or more motion sensors.

14. A method in an apparatus for measuring cardiac activity of a user, the method comprising:
   obtaining a cardiac activity measurement signal from an optical cardiac activity sensor unit configured to be placed against a body tissue of the user, the optical cardiac activity sensor unit comprising a first light emitting element configured to emit light having a first wavelength, a second light emitting element configured to emit light having a second wavelength, and a third light emitting element configured to emit light having a third wavelength;
   obtaining, via the optical cardiac activity sensor unit, a first signal caused by the emitted light having the first wavelength, a second signal caused by the emitted light having the second wavelength, and a third signal caused by the emitted light having the third wavelength;
obtaining a bioimpedance measurement signal utilizing a plurality of electrodes configured to be placed against the body tissue;
detecting changes in the bioimpedance measurement signal; and
reducing, based on performing a subtraction operation or an addition operation between the first signal and the second signal and the third signal, a motion artefact effect, caused by a movement between the optical cardiac activity sensor unit and the body tissue, on the cardiac activity measurement signal,
wherein the reducing the motion artefact effect on the cardiac activity signal is further based on adjusting direct current levels of the first, second, and third signals to the same direct current level before the addition operation or the subtraction operation.

15. A non-transitory computer readable medium comprising program instructions which when loaded into an apparatus cause the apparatus to perform a method comprising:
obtaining a cardiac activity measurement signal from an optical cardiac activity sensor unit configured to be placed against a body tissue of the user, the optical cardiac activity sensor unit comprising a first light emitting element configured to emit light having a first wavelength, a second light emitting element configured to emit light having a second wavelength, and a third light emitting element configured to emit light having a third wavelength;
obtaining, via the optical cardiac activity sensor unit, a first signal caused by the emitted light having the first wavelength, a second signal caused by the emitted light having the second wavelength, and a third signal caused by the emitted light having the third wavelength;
obtaining a bioimpedance measurement signal utilizing a plurality of electrodes configured to be placed against the body tissue;
detecting changes in the bioimpedance measurement signal; and
reducing, based on performing a subtraction operation or an addition operation between the first signal and the second signal and the third signal, a motion artefact effect, caused by a movement between the optical cardiac activity sensor unit and the body tissue, on the cardiac activity measurement signal,
wherein the reducing the motion artefact effect on the cardiac activity signal is further based on adjusting direct current levels of the first, second, and third signals to the same direct current level before the addition operation or the subtraction operation.

* * * * *